US010327819B2

(12) United States Patent
Sekhon

(10) Patent No.: US 10,327,819 B2
(45) Date of Patent: Jun. 25, 2019

(54) BONE SCREW

(71) Applicant: Nevada Neurosurgery, Reno, NV (US)

(72) Inventor: Lali Sekhon, Reno, NV (US)

(73) Assignee: Nevada Neurosurgery, Reno, NV (US)

( * ) Notice: Subject to any disclaimer, the term of this patent is extended or adjusted under 35 U.S.C. 154(b) by 148 days.

(21) Appl. No.: 15/535,783

(22) PCT Filed: Dec. 16, 2015

(86) PCT No.: PCT/US2015/066194
§ 371 (c)(1),
(2) Date: Jun. 14, 2017

(87) PCT Pub. No.: WO2016/100570
PCT Pub. Date: Jun. 23, 2016

(65) Prior Publication Data
US 2017/0360480 A1  Dec. 21, 2017

Related U.S. Application Data

(60) Provisional application No. 62/092,740, filed on Dec. 16, 2014.

(51) Int. Cl.
A61B 17/70 (2006.01)
A61B 17/86 (2006.01)
A61B 17/88 (2006.01)
A61B 17/16 (2006.01)
A61B 17/00 (2006.01)

(52) U.S. Cl.
CPC ...... *A61B 17/7032* (2013.01); *A61B 17/1604* (2013.01); *A61B 17/1642* (2013.01); *A61B 17/1671* (2013.01); *A61B 17/7082* (2013.01); *A61B 17/8625* (2013.01); *A61B 17/8635* (2013.01); *A61B 17/8685* (2013.01); *A61B 17/8872* (2013.01); *A61B 2017/0042* (2013.01); *A61B 2017/8655* (2013.01)

(58) Field of Classification Search
CPC ............ A61B 17/7032; A61B 17/1642; A61B 17/1671; A61B 17/7082; A61B 17/8625; A61B 17/8635; A61B 17/8685; A61B 2017/0042; A61B 2017/8655
See application file for complete search history.

(56) References Cited

U.S. PATENT DOCUMENTS

| 4,790,303 | A  | 12/1988 | Steffee |
| 4,887,596 | A  | 12/1989 | Sherman |
| 5,207,678 | A  | 5/1993  | Harms et al. |
| 7,037,309 | B2 | 5/2006  | Weil et al. |
| 9,089,371 | B1 | 7/2015  | Faulhaber |

(Continued)

OTHER PUBLICATIONS

European Patent Office, "Extended European Search Report", European patent application No. 15871023.6, dated Jul. 23, 2018.

(Continued)

Primary Examiner — Olivia C Chang
(74) Attorney, Agent, or Firm — IpHorgan Ltd.

(57) ABSTRACT

A bone screw, such as a pedicle screw, comprises an anchor portion and a sleeve portion, the anchor portion including an angled or curved portion and an externally threaded portion. The sleeve portion having an external thread for engaging bone, and a threaded internal bore for engaging the externally threaded portion of the anchor portion.

17 Claims, 27 Drawing Sheets

(56) References Cited

U.S. PATENT DOCUMENTS

| | | |
|---|---|---|
| 9,579,123 B2 | 2/2017 | Faulhaber |
| 9,844,396 B2 | 12/2017 | Faulhaber |
| 2005/0143735 A1 | 6/2005 | Kyle |
| 2005/0182409 A1 | 8/2005 | Callahan et al. |
| 2007/0299450 A1 | 12/2007 | Her et al. |
| 2008/0015586 A1 | 1/2008 | Krishna et al. |
| 2010/0016903 A1* | 1/2010 | Matityahu ............ A61B 17/866 606/301 |
| 2014/0107712 A1 | 4/2014 | Fallin et al. |
| 2014/0142575 A1 | 5/2014 | Biedermann et al. |
| 2018/0064468 A1 | 3/2018 | Faulhaber |

OTHER PUBLICATIONS

Chao, C.K., Increasing Bending Strength and Pullout Strength in Conical Pedicle Screws: Biomechanical Tests and Finite Element Analyses, J. Spinal Disorders & Techniques, 2008, p. 130-138, vol. 21(2).

* cited by examiner

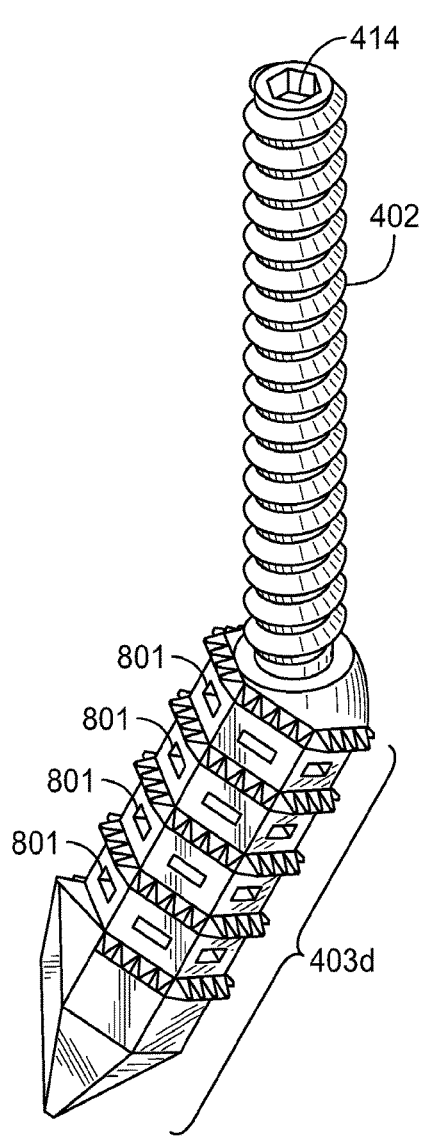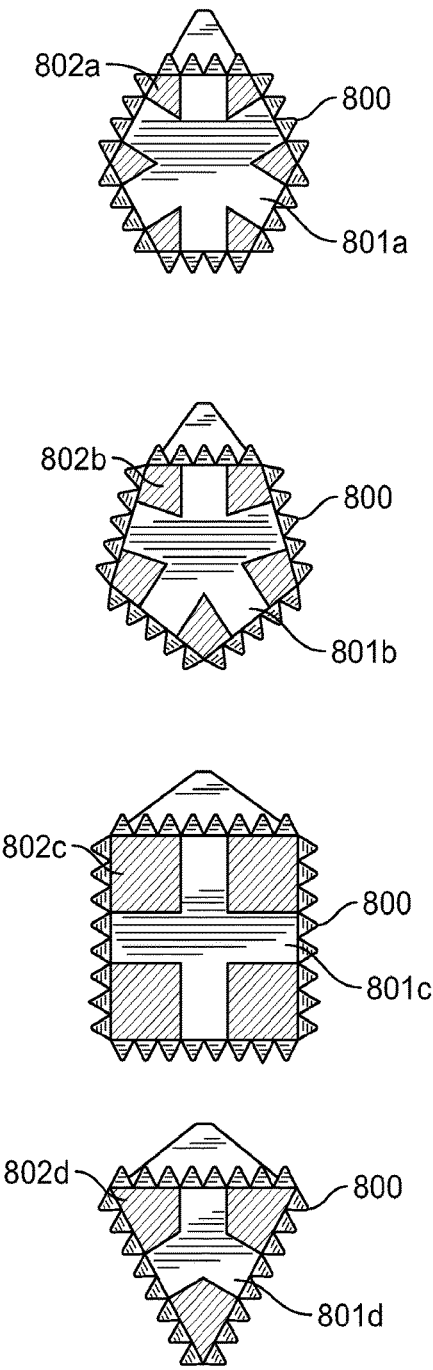
FIG. 8B
FIG. 8C

BONE SCREW

CROSS REFERENCE TO PRIOR APPLICATIONS

The present application is the national stage entry of International Application No. PCT/US2015/066194, filed on Dec. 16, 2015, and claims the benefit of U.S. Provisional Application No. 62/092,740, filed on Dec. 16, 2014, the entire contents of which are incorporated herein by reference.

FIELD OF THE DESCRIPTION

The present description relates to bone anchoring devices. In particular, the description relates to a bone screw, such as a pedicle screw for spinal fixation.

BACKGROUND OF THE DESCRIPTION

Various devices and prostheses have been proposed to correct and/or stabilize spinal injuries or deformities. Such devices include artificial spinal discs, nuclei etc. Such devices serve to replace existing damaged or diseased portions of the spine. In some cases however, it is desirable or necessary to fuse spinal vertebrae so as to prevent or reduce any movement. Such fixation devices commonly utilize pedicle screws that are implanted into the pedicles of vertebrae and serve as anchors for other prosthetic devices. FIGS. 1 and 2 illustrate a vertebral segment 100 with pedicles 102a and 102b that extend from the vertebral body 101. FIG. 2 illustrates the placement of pedicle screws 200 as known in the art. Such pedicle screws 200 have a threaded portion 208 that is screwed into the pedicle and head portions 204 and 206 respectively that connect to other fixation devices such as a rod 206.

Pedicle screw fixation systems have been used in providing spinal stabilization and spinal fusion in patients with a variety of conditions such as degenerative spondylolisthesis, isthmic spondylolisthesis, fusion after decompression, spinal fractures, and surgically repaired spinal pseudoarthroses. The advent of rigid pedicle screw/rod fixation devices has led to a dramatic increase in the rate of arthrodesis (i.e. the surgical fusion of a joint) particularly for the treatment of degenerative disc disease and spondylolisthesis. In addition to higher rates of arthrodesis, rigid instrumentation has enabled surgeons to maintain, improve, or fully reduce spondylolisthesis outright, and these devices have allowed for very aggressive strategies for decompression.

As shown in FIG. 2, typical pedicle screw fixation systems as known in the art are multi-component devices consisting of solid rods 206 that are longitudinally interconnected and anchored to adjacent vertebrae using pedicle screws such as pedicle screw 200. The screws and other components are generally made of stainless steel, titanium or other acceptable implantable material, typically metal alloys. The surgeon selects from among these components to construct a system suitable for a patient's anatomical and physiological requirements. Pedicle screws are similar to the screws used in long bones.

During implantation, pedicle screws are inserted into channels that are drilled or otherwise formed through the cancellous central axis of each vertebral pedicle 102a and 102b. The longitudinal connecting rods 206 usually span and brace two or more vertebrae and, as mentioned above, are connected to the screws 200. Each vertebra typically receives a pedicle screw in both pedicles. The connecting rods 206 are provided in pairs with each of the rods extending over one side of the spine.

The screws hold their purchase within the bones through several mechanisms. One of the main sources of pullout resistance is obtained by the use of screw threads. The use of threads allows for better fixation due to increased contact area with the surrounding bone material. It is understood in the current art that placement of the screw in a manner such that it is directed towards the median plane of the vertebrae improves pullout resistance by allowing the screw to interact with a greater amount of bone material.

Insufficient resistance against pullout of the bone screws is a recognized problem with current bone screws. This problem is faced in cases of poor bone quality such as in those patients with osteoporosis. Fixation of a screw into bone is directly related to the amount of contact area between the bone and the screw, as well as the quality of that contact. Therefore, the more direct contact there is between the bone and the surface of the screw, the better the purchase and fixation. A long screw with a large diameter will provide better fixation than a short screw with a lesser diameter as a result of the larger surface contact area of the larger screw. Also, the density of the bone determines the actual real contact surface between screw and bone, as bone with a high density will have more bone material in direct contact with the available screw surface than bone with lower density. Thus, in patients with osteoporosis where the bone mineral density is low, there is less surface contact between the screw and bone than in patients with normal bone mineral density.

Screw loosening as a result of constant back and forth toggling forces acting on the screw is also a cause for screw pullout. These forces can occur during regular flexion and extension motions of the spine (Chao, C. K. et al. *Increasing Bending Strength and Pullout Strength in Conical Pedicle Screws: Biomechanical Tests and Finite Element Analyses.* J. Spinal Disorders & Techniques. 2008. 21 (2): 130-138, 2008).

Examples of known pedicle screws are provided in U.S. Pat. Nos. 4,887,596 and 5,207,678. Some more recent screws and screw systems have been proposed to address specific issues. For example, a cannulated pedicle screw is provided in US publication number US2007/0299450. In this reference, the pedicle screw is provided with a central cannula or canal having an opening at the distal end of the screw. Once implanted, bone cement is injected into the cannula and into the joint between the screw and the bone.

U.S. Pat. No. 7,037,309 provides another cannulated pedicle screw having a self-tapping distal tip. A screw of this type avoids the need for boring hole prior to insertion of the screw.

US publication numbers US2005/0182409 and US2008/0015586 teach a device for dynamic stabilization of the spine and are directed to the problem of shear stresses on pedicle screws. In these references, the devices include pedicle screws that are provided with a head that connects to moveable elements. In the course of regular motion, such elements are adapted to absorb compressive or expansive forces and to thereby reduce the amount of stresses translated to the screws. The moveable elements are often complicated devices as compared to the commonly known rods.

There is a need for a bone screw that resists pullout.

SUMMARY OF THE DESCRIPTION

In one aspect, the present description provides a bone screw, in particular a pedicle screw which comprises an anchor portion and threaded sleeve portion adapted to engage the anchor portion. The anchor portion comprises an angled, nail portion and a threaded portion that are angled in relation to one another. The threaded sleeve comprises an external thread and a threaded internal bore. The threaded sleeve is adapted to be screwed onto the threaded portion of the anchor portion. The threaded sleeve has a sleeve head at its proximal end which is adapted to be engaged with a screw head. The screw head is adapted to engage with fixation devices such as rods.

Prior to insertion of the pedicle screw a channel can be created though the pedicle and into the vertebral body of the vertebra to facilitate the placement of the pedicle screws. The pedicle screw can then be inserted whereby the angled portion is impacted into place, followed by the threaded sleeve being threaded onto the treaded portion of the anchor portion and the screw head engaged onto the sleeve head to facilitate the attachment of fixation devices.

In one embodiment the sleeve head and the screw head are engaged in a manner such that they form a ball and socket joint. The ball and socket joint allows the screw head to swivel while engaged to the sleeve head. In another embodiment the angled, nail portion is provided with a protrusion to act as a further anchor for the nail portion into the vertebra to resist pullout. In a further embodiment the angled portion of the anchor portion may be provided with surface medication to allow for an increased amount of surface area of the nail portion in contact with surrounding bone material. The surface modifications can also further act as anchors for the nail portion into the vertebra. Such surface modifications can include studs and raised ridges. In further embodiments the angled portion has fenestrations that promote bony ingrowth into them. Such bony ingrowth further locks the nail portion into the vertebra.

BRIEF DESCRIPTION OF THE DRAWINGS

The features of the description will become more apparent in the following detailed description in which reference is made to the appended drawings wherein:

FIG. 8B is a perspective view of the pedicle screw of FIG. 8A;

FIG. 8C is a cross sectional views of alternate embodiments for the pedicle screw of FIG. 8A across the line D-D;

DETAILED DESCRIPTION

Figure 1:
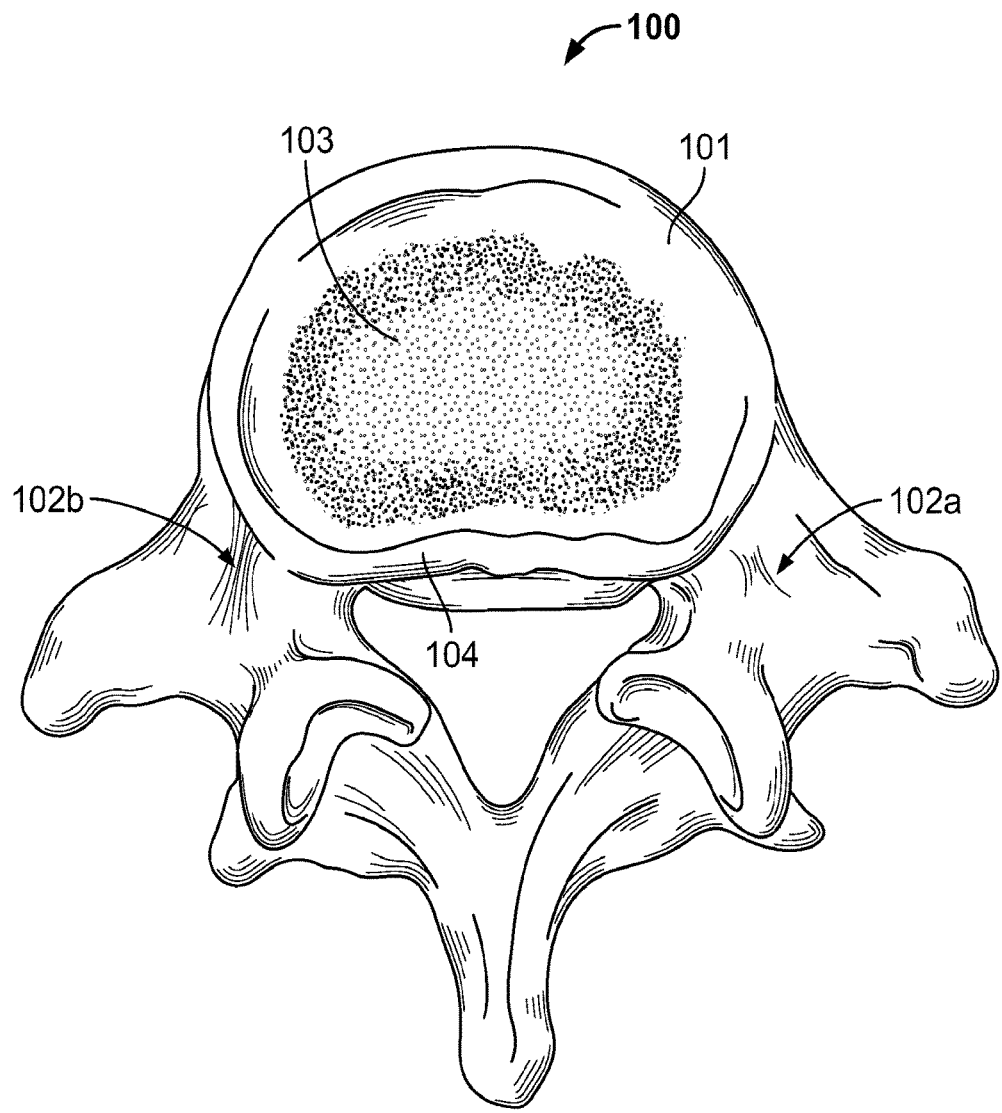
FIG. 1 is a plan view of a spinal vertebra.

The following description is provided with reference to various embodiments thereof. The description will refer primarily to pedicle screws and to spinal stabilization. However, it will be understood by persons skilled in the art that the screw described herein can be utilized in and/or for any bone anchoring or fixation application. Thus, the references herein to pedicle screws and to spinal fixation or fusion will be understood as being illustrative of a particular aspect of the description and are not intended to limit the description in any way. The bone screw described herein can, for example, be used in applications involving large bones such as the femur, tibia, fibula, ulna, etc. as well as for attaching cervical plates and cages to cervical vertebrae. Thus, all references herein to "pedicle screws" will be understood as meaning a bone screw according to an aspect of the description wherein the screw is used for securing into a pedicle. It will be understood that the following description will be made with reference to the accompanying figures and elements shown therein and that such elements will be identified with one or more reference numerals. Unless indicated otherwise, the characteristics or features of any of the elements will be understood to apply to all equivalent elements, indicated as being such, regardless of any difference in the reference numerals used to identify same.

In the present description, the terms "distal" and "proximal" are used. These terms are used for convenience only and are not intended to limit the description in any way. The term "distal" will be used in relation to that end of the screw of the description that is inserted into bone. The term "proximal" will be used to refer to the opposite end of the screw that extends outside of the bone into which the screw is implanted. Thus, although these descriptive terms are used to describe the present screws in reference to their placement in bone, it will be understood that the description is not limited to screws solely when in use or solely when combined with bone.

The terms "posterior" and "anterior" will be used herein in terms of the orientation of the spine in a mammal, such as a human. It will be understood that such terms are used purely to facilitate the description of the present bone screw and not to limit the screw in any way.

As will be known in the art, a spine comprises a plurality of vertebrae. FIG. 1 shows a plan view of a typical spinal vertebra 100. The vertebra 100 includes a vertebral body 101 which is mainly comprised of a core of cancellous bone 103. The outer portions of the vertebral body 101 are dense cortical bone 104, which is harder than cancellous bone 103. The posterior portion of the vertebra 100 is connected to the vertebral body 101 by pedicles 102a and 102b. The pedicles are formed of tough cortical bone on the outside and softer cancellous bone within.

Figure 2:
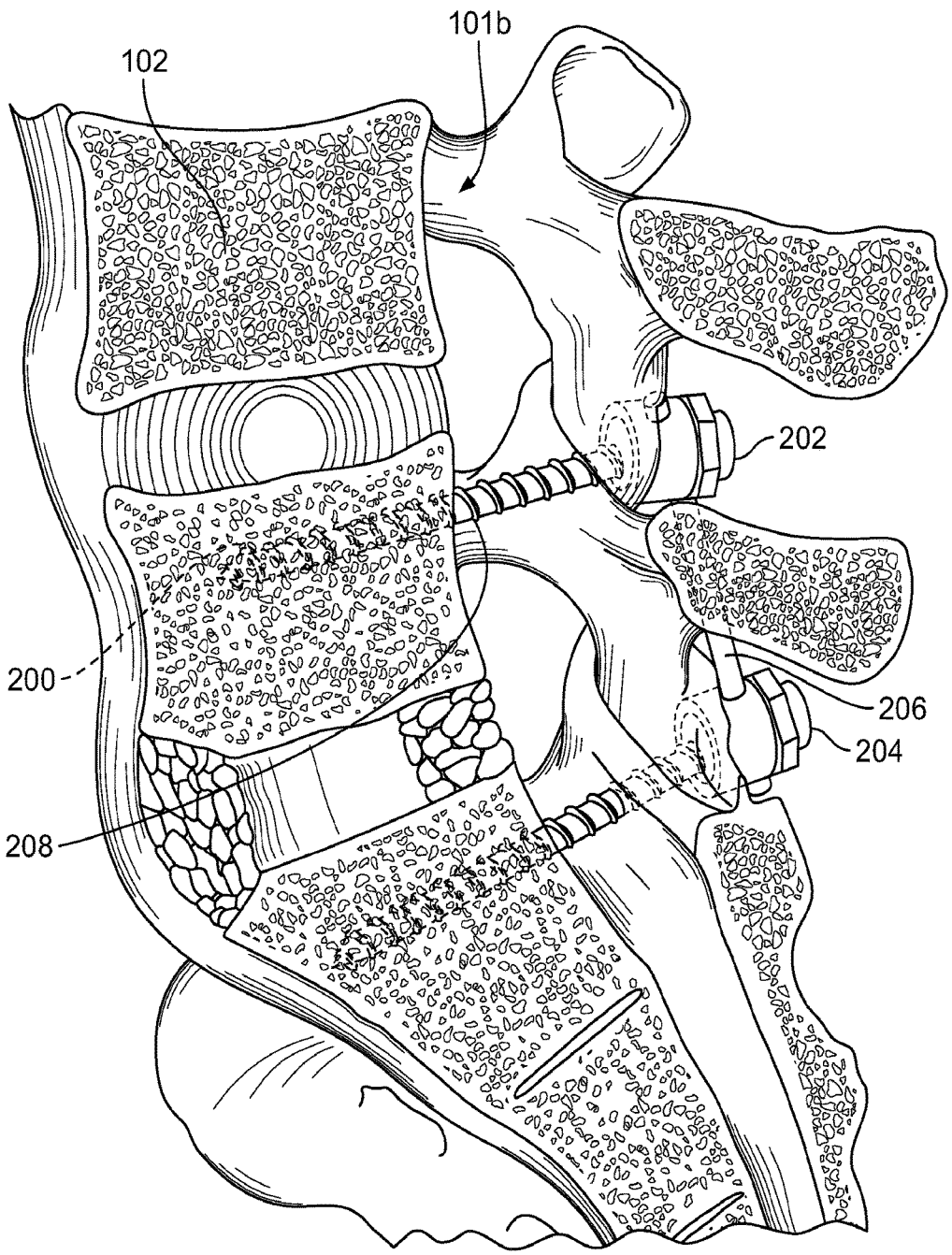
FIG. 2 is a sagittal cross-sectional elevation of a spinal segment incorporating pedicle screws of the prior art.

FIG. 2 is a sagittal cross sectional view of a spinal section showing adjacent lumbar vertebrae into which pedicle screws 200 of a known design are implanted. The screws have heads 202 and 204 respectively. As shown, each of the pedicle screws 200 is inserted through a respective pedicle 102a and 102b and into the cancellous bone 103 of the vertebral body 101. Two pedicle screws are inserted into separate vertebral bodies. The heads 202 and 204 of the screws 200 are connected to rods 206 in order to stabilize the two adjacent vertebrae. The stabilization is made possible as the screws and rods create a solid "brace" to hold the vertebrae in place. Their combination inhibits movement from occurring between the vertebrae and thus increases stability.

Figure 3:
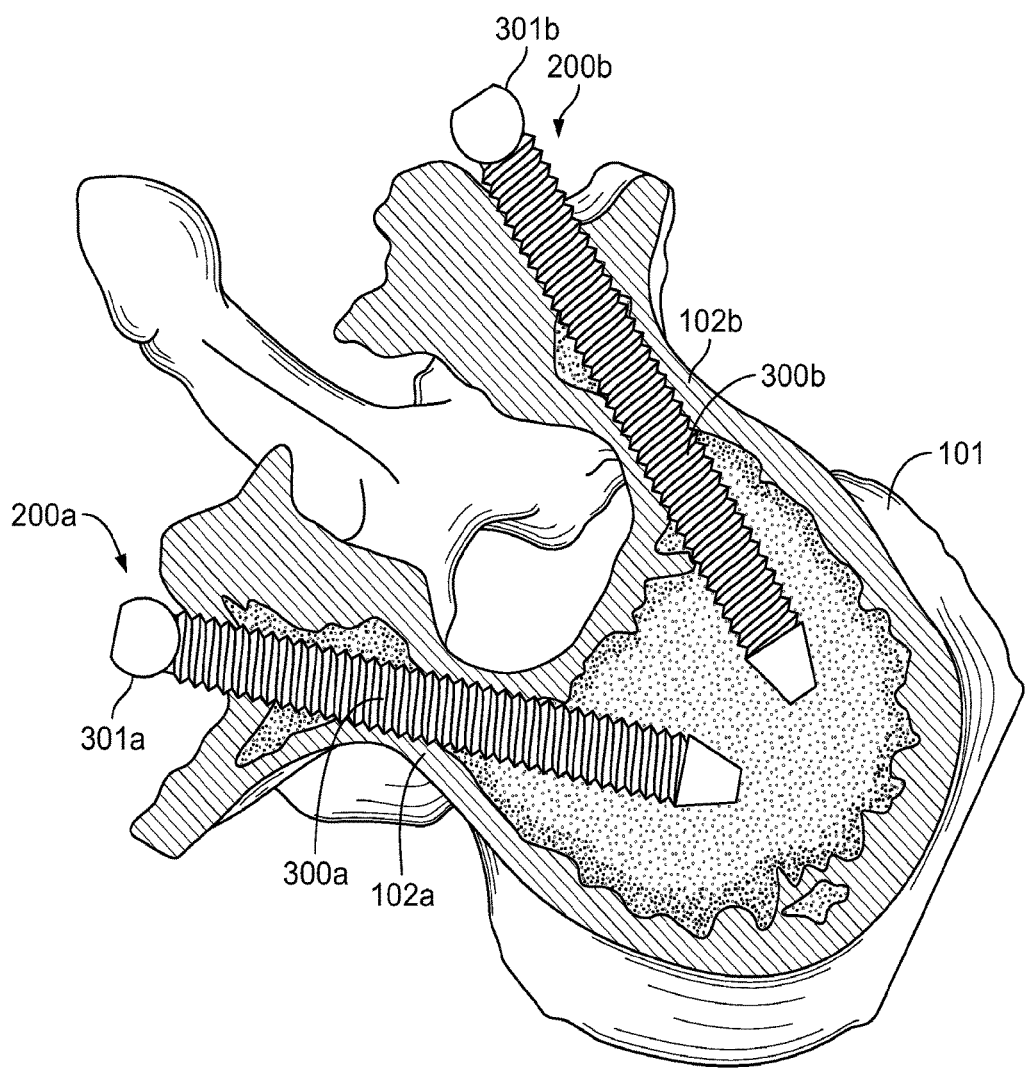
FIG. 3 is a horizontal cross-sectional view of a vertebra with two prior art pedicle screws.

As seen in FIG. 3 two prior art pedicle screws 200a and 200b are engaged into a vertebral body 101. As shown, each of the pedicle screws passes through a respective pedicle 102a and 102b. The bodies of the prior art pedicle screws 200a and 200b consist mainly of threaded portions 300a and 300b respectively. The screws also have proximal portions 301a and 302b which can be spherical, such as to connect with heads 202 and 204, which in turn facilitate connection to rods 206, as shown in FIG. 2.

As can be seen, the screws 200a and 200b are inserted through the pedicles 102a and 102b and into the vertebral body 101. This makes use of the anatomical structure of the vertebra and increases contact area between the bone and pedicle screws in order to resist screw pullout.

Figure 4A:
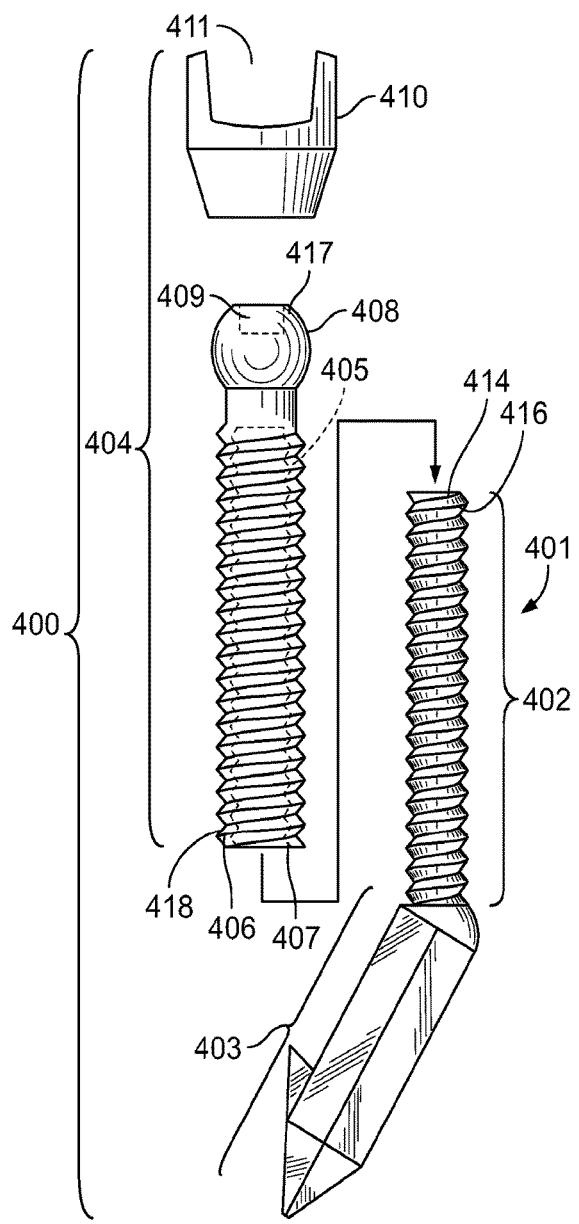
FIG. 4A is an exploded side view of a pedicle screw according to an embodiment as described herein.
Figure 4B:
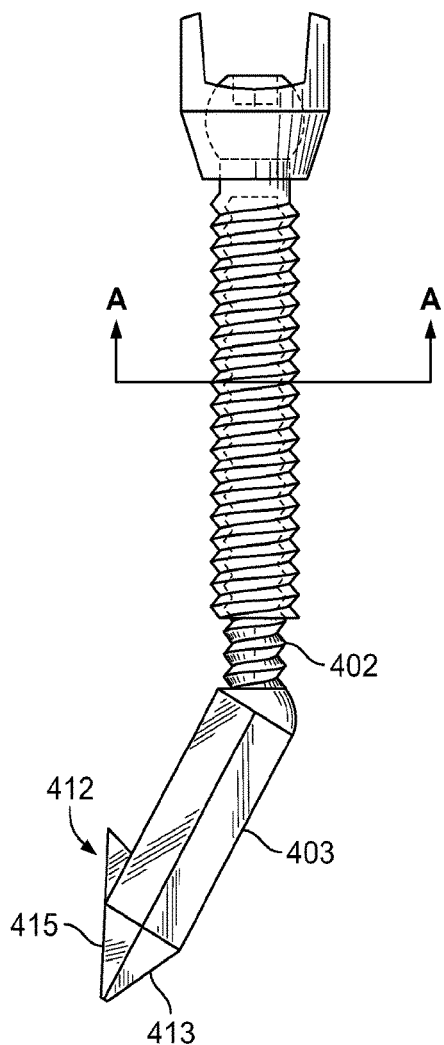
FIG. 4B is a side view of the pedicle screw of FIG. 4A in an assembled state.

In FIGS. 4A and 4B, the components of a pedicle screw 400 according to one aspect of the description are shown. The pedicle screw 400 comprises an anchor portion 401 and a threaded sleeve 404. The anchor portion 401 consists of a distal angled or nail portion 403 and a proximal threaded portion 402. The proximal threaded portion 402 is comprised of a shaft having an external thread. In one embodiment as illustrated in FIG. 4, the angled or nail portion 403 comprises in the illustrated embodiment a square cross section but other cross sections are possible, as discussed below. The angled or nail portion 403 may also include a tip, such as a pointed tip 413 at the distal end 415. The tip 413 is preferably provided to aid in the insertion of the nail portion 403 into a vertebra 100. It will be understood that in some embodiments, the pointed tip 41 may be omitted or replaced with another feature offering the same functionality. From the present description, it will also be understood that the nail portion serves as an anchor for the bone screw.

The longitudinal axis of the angled or nail portion 403 and the longitudinal axis of the threaded portion 402 are angled in relation to one another. As discussed further below, various degrees of angulation may be provided between the angled or nail portion 403 and the threaded portion 402.

The angled or nail portion 403 may in one embodiment be provided with a protrusion 412 at the distal end 415. As discussed further below, the protrusion 412 serves to increase the anchoring force when implanted in bone, such as vertebra 100 for the pedicle screw 400, particularly once bone regrowth has occurred post-implantation of the screw 400.

Figure 6A:
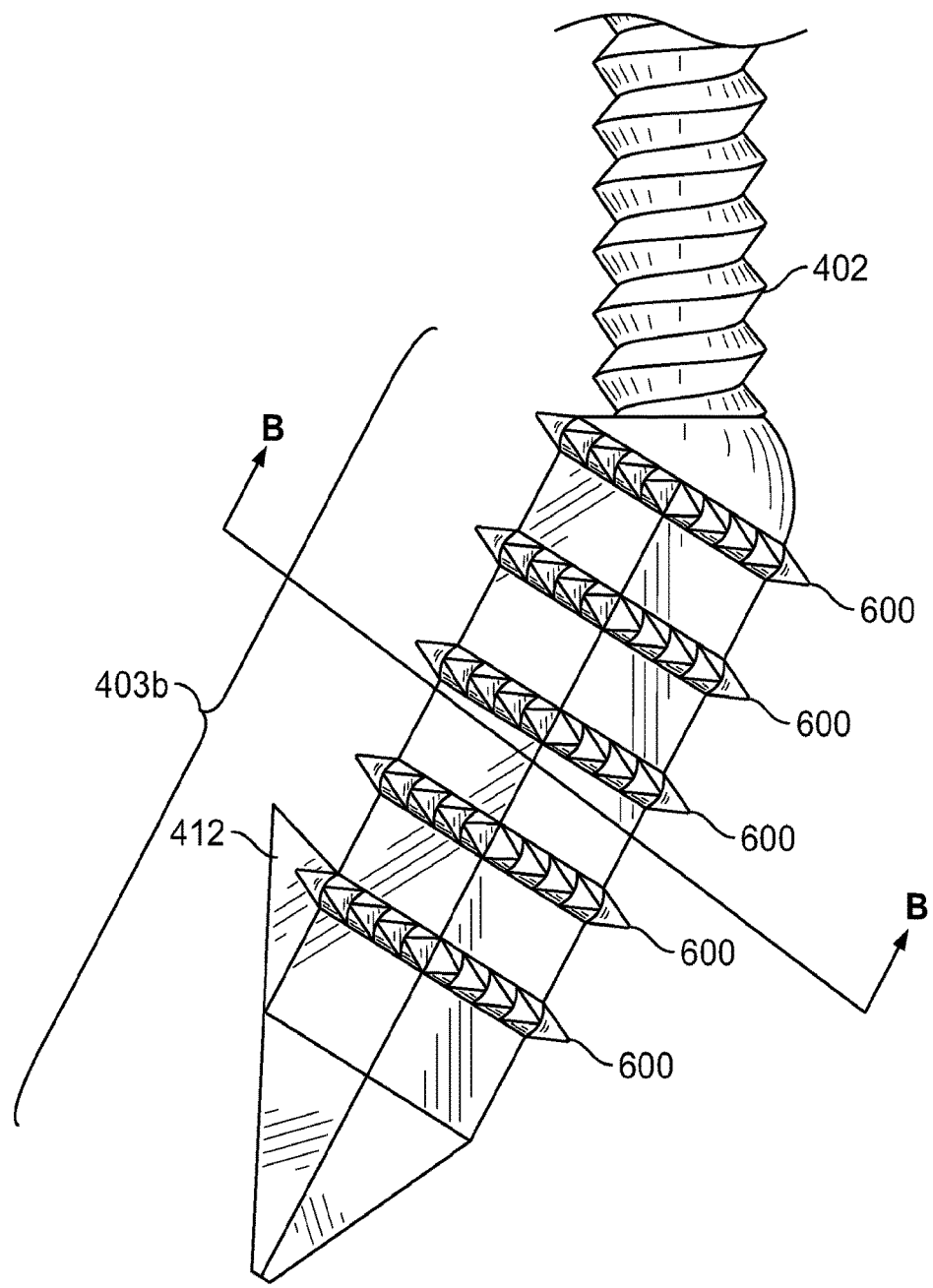
FIG. 6A is a side view of the distal portion of the pedicle screw according to an embodiment.
Figures 6B, 6C:
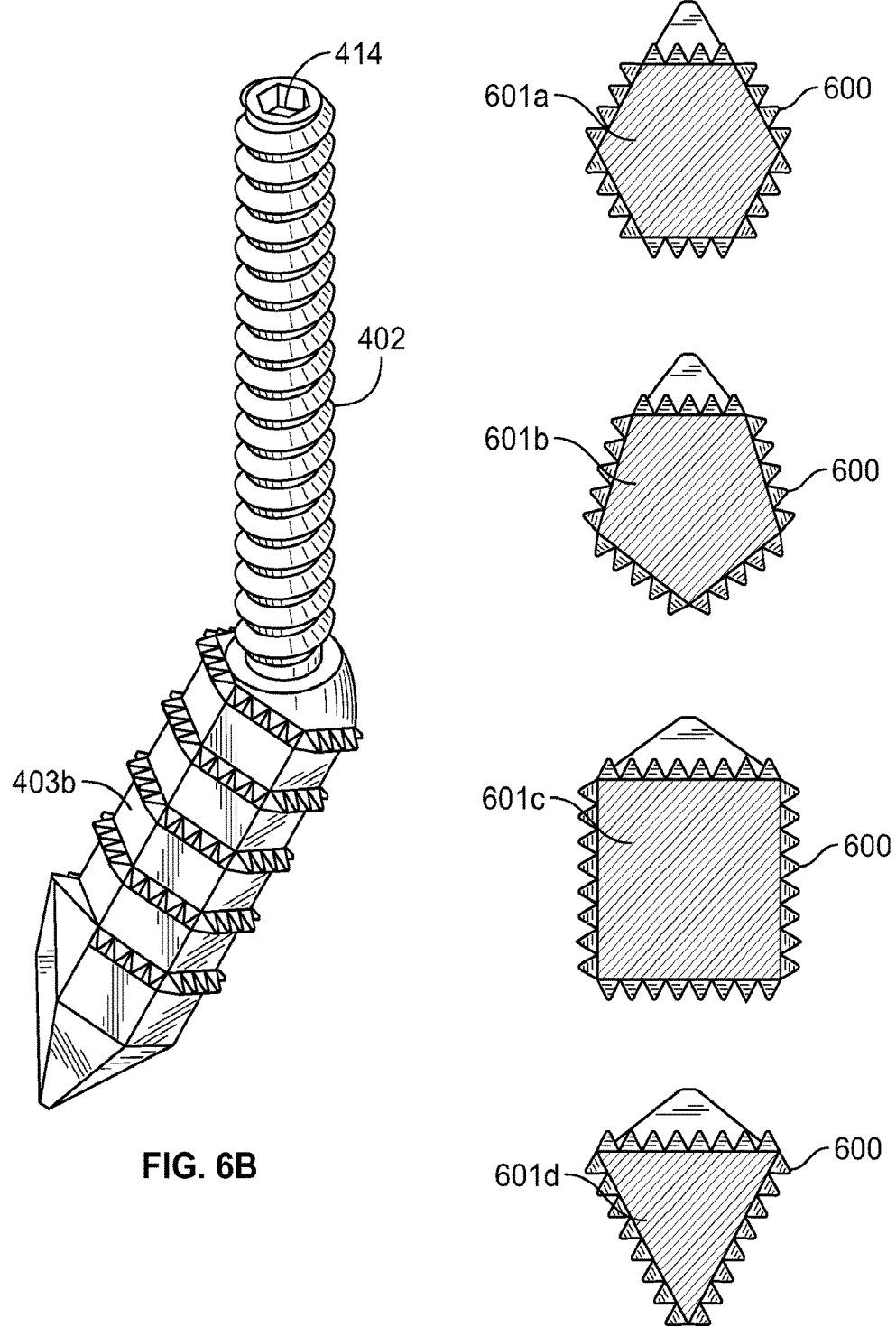
FIG. 6B is a perspective view of the pedicle screw of FIG. 6A.
FIG. 6C is a cross sectional view taken along line B-B of FIG. 6A showing alternate embodiments of the pedicle screw.

The threaded portion 402 of the nail portion 401 may include a recess 414 to receive a setting tool for stabilizing the anchor portion 401. The setting tool may also be used to guide the threaded sleeve 404 during insertion. One example of the recess 414 is shown in FIG. 6B, wherein the recess 414 is shown as having a hexagonal shape. As will be understood, the shape of recess 414 is adapted to accommodate the shape of the setting tool. Thus, as will be understood, the recess 414 may be provided in any other shape. Another means of stabilizing the anchor portion is discussed below with respect to FIGS. 21A to 21H.

Figure 10:
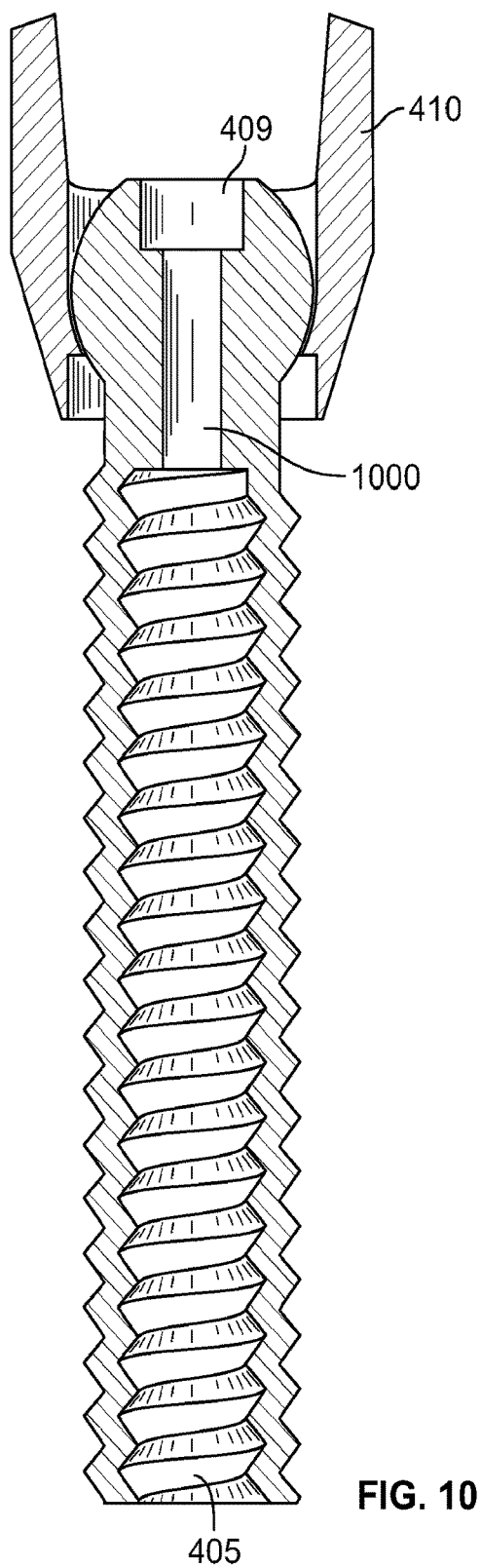
FIG. 10 is a longitudinal side cross sectional view of the proximal portion of the pedicle screw.

The threaded sleeve 404 has a proximal end 417 and a distal end 418. The threaded sleeve has an external thread 406 on its outer surface and an internal bore 405 which may extend between the distal end 418 and the proximal end 417 of the threaded sleeve 404. The wall of the internal bore 405 is threaded by a thread referred to herein as an internal thread 407. The external thread 406 extends between the distal end 418 and the proximal end 417 of the threaded sleeve 404. The threaded sleeve 404 may also have a screw head 410 engaged to the sleeve head 408. In the illustrated embodiment, the sleeve head 408 is shown as being generally spherical in shape, which is particularly advantageous since, as also shown in the figures, the sleeve head 408 and the screw head 410 form a ball and socket joint, as shown in FIG. 10. In this manner, the screw head 410, according to this embodiment, is allowed to move in various directions while being connected to the sleeve head 408. It will be understood that the sleeve head 408 may be provided with any variety of shapes.

Figure 18:
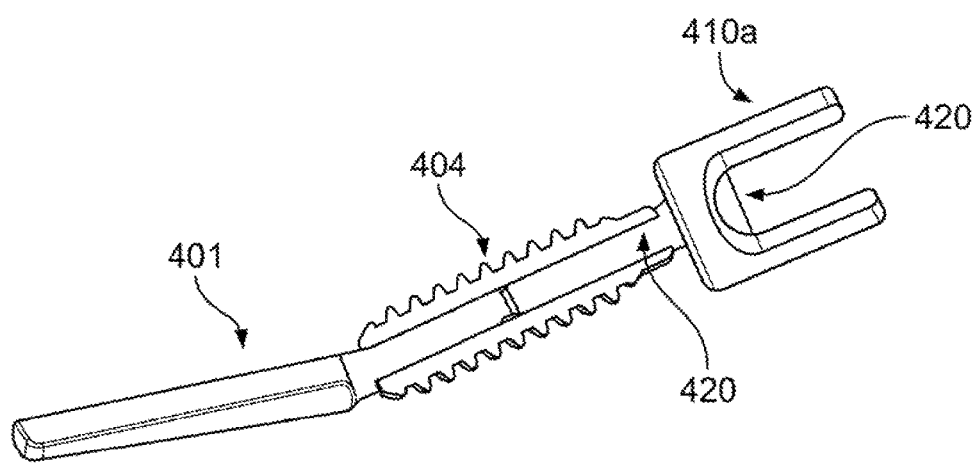
FIG. 18 is a schematic side view of another embodiment of the described bone screw.

In other aspects, the screw head 410 may be integrally formed with the sleeve 404 so as to be a formed part of sleeve head 408. In other aspects, the screw head may be a separate component that is connected to the sleeve head 408 prior to or during insertion of the screw into bone or later. The screw head 410 may, for example, be threaded onto the sleeve head 408. For example, in one aspect, as illustrated in FIG. 18, the screw head 410a may include a post portion 420 that is inserted into the sleeve 404. In one aspect, such a post 420 may be provided with an external thread that is adapted to cooperate with the internal thread of the sleeve 404. The head 410a may be secured to the post in any way.

The sleeve head 408 may include an aperture 409 to permit the passage of a tool that can be used for placement of screw 400 into the vertebra 100. A passage 1000 comprises an open channel extending between the aperture 409 and the threaded internal bore 405, as shown in FIG. 10. The passage 1000 allows for tools to pass through the aperture 409 and into the threaded internal bore 405. The radius of the passage 1000 may be varied depending on the tools used for placement of the anchor portion 401 and threaded sleeve 404 into the vertebra 100. The internal threads 407 are adapted to engage the threads of the threaded portion 402. The radius of the internal bore 405 is large enough to accommodate insertion of the threaded portion 402 of the anchor portion 401 into the bore 405 as the internal threads 407 are threaded onto the threaded portion 402. In a preferred embodiment, the bore 405 is adapted to receive the entire length of the threaded portion 402 of the anchor portion 401.

The screw head 410 comprises a recess 411 or other such feature that enables the head 410 to engage a fixation device as known in the art. For example, the fixation device may comprise rods 206 as described above. The description is not limited to the types of fixation devices that may be used. Similarly, the description is not limited to any particular form or function of the screw head 410.

A method for inserting the pedicle screw 400 into the vertebra 100 will now be discussed according to one aspect of the description. Generally, insertion, or implantation, of the screw 400 into a vertebra comprises a two-step procedure. First, the anchor portion 401 is inserted through a pedicle such as either pedicle 102a or 102b and into a vertebral body 101. Second, the threaded sleeve 404 is implanted, by threading the sleeve 404 onto the threaded portion 402 of the anchor portion 401. As will be understood, as the threaded sleeve 404 is implanted, the external threading provided thereon engages the bone of the pedicle. Once the screw 400 is thus implanted, bone is allowed to re-form about the screw in a normal healing process. As will be understood, such bone re-growth step will increase the hold of the screw within the vertebra.

In a preferred embodiment, prior to the insertion of the anchor portion 401, a channel for the anchor portion 401 is first created through the pedicle and the vertebral body to help facilitate the insertion of at least the anchor portion 401. In one embodiment, such a channel is created by removing bone material using a tool, such as a pedicle probe 1600 as shown in FIG. 16. In this example, the channel is created by using the distal end 1601 of the pedicle probe 1600 to penetrate and remove or excavate bone material in the vertebra 100 along a path to enable the anchor portion 401 to be inserted. As will be understood, creating a channel as described above facilitates the insertion of the screw 400 by creating a passage for the insertion of the anchor portion 401 into the vertebra 100.

The anchor portion 401 is inserted into the vertebra 100 by applying a force at its proximal end 416 to drive it into the vertebra 100. This force can, for example, be generated by hammering the proximal end 416 by using a suitable surgical tool as known in the art. In one embodiment, the anchor portion 401 is inserted into the vertebra 100 through the passage created by the pedicle probe 1600. The anchor portion 401 is inserted through the pedicle 102a or 102b and into the vertebral body 101. The pointed tip 413 at the distal end 415 of the anchor portion 401 facilitates the insertion of the anchor portion 401 through the channel. The shape of the pointed tip 413 reduces resistance faced by the anchor portion 401. As bone within the vertebra 100 repairs and new bone material grows, the bone material grows around, for example, the angled or nail portion 403 of the anchor portion 401. Thus, when the protrusion 412 is surrounded by bone material it along with the rest of the angled or nail portion 403 acts to further anchor the screw 400 within the bone material. As will be understood, such an anchoring results in an increased resistance to pullout forces for the anchor portion 401. Similarly, bone re-growth also occurs around the various threaded surfaces of the screw 300 that are exposed to the bone of the vertebra, thereby also increasing the pullout resistance of the screw. Various chemical or other treatments may also be used on portions of the screw and nail portions etc. to further enhance the anchoring of the screw within the bone. As will be understood, the anchor portion 401, and in particular the angled or nail portion 403, may be referred to as an anchor for the subject bone screw.

As the anchor portion 401 is inserted into the vertebra 100, it is desired to insert most if not all of the angled or nail portion 403 into the vertebral body 101. The threaded portion 402 is housed within the pedicle, such as either pedicle 102a or 102b. In the preferred embodiment the entire threaded portion 402 is inserted into the pedicle however a portion may extend out of the pedicle.

Figure 11:
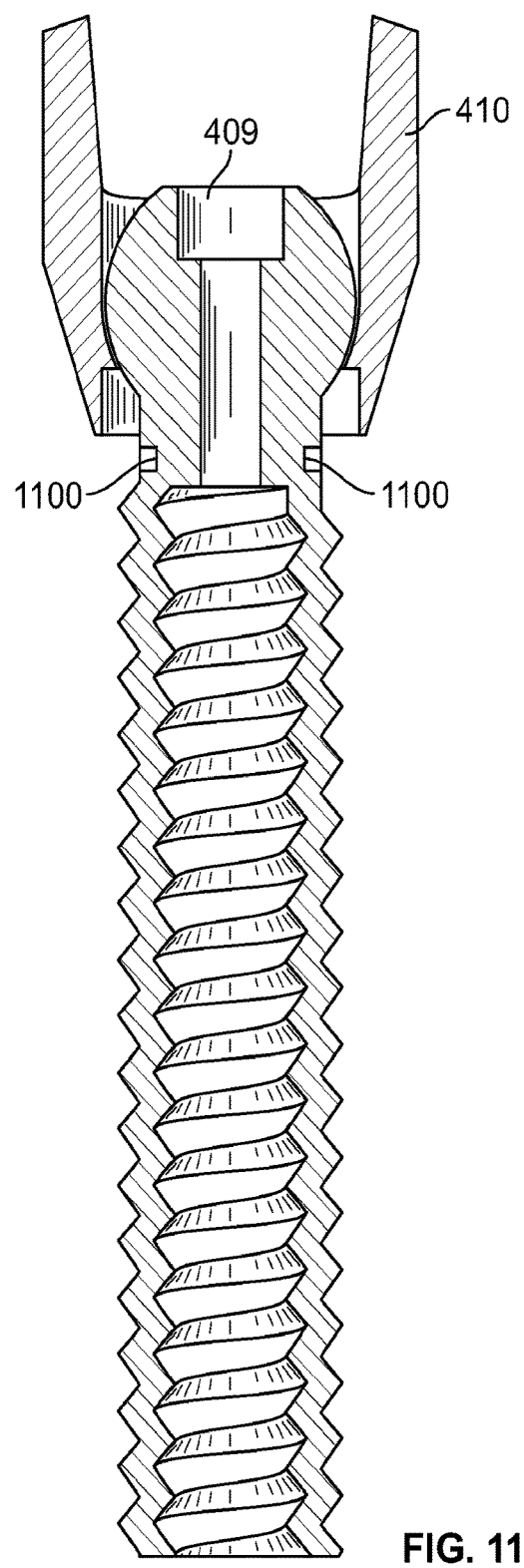
FIG. 11 is a longitudinal cross sectional view of the proximal portion of the pedicle according to another embodiment.
Figure 12:
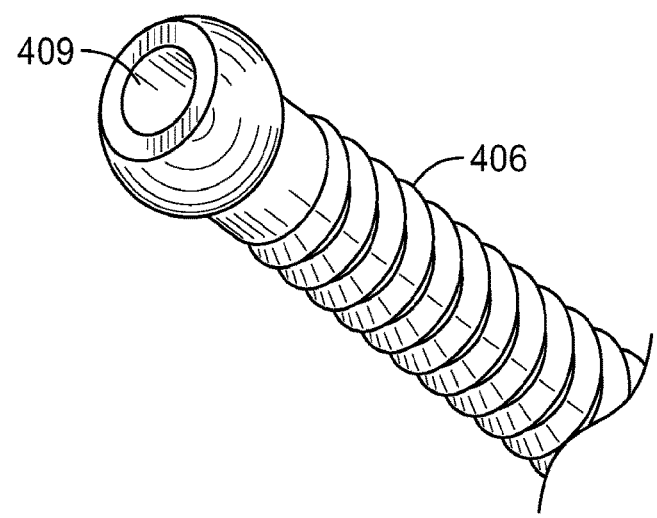
FIG. 12 is a perspective view of the proximal portion of the pedicle screw.
Figure 13:
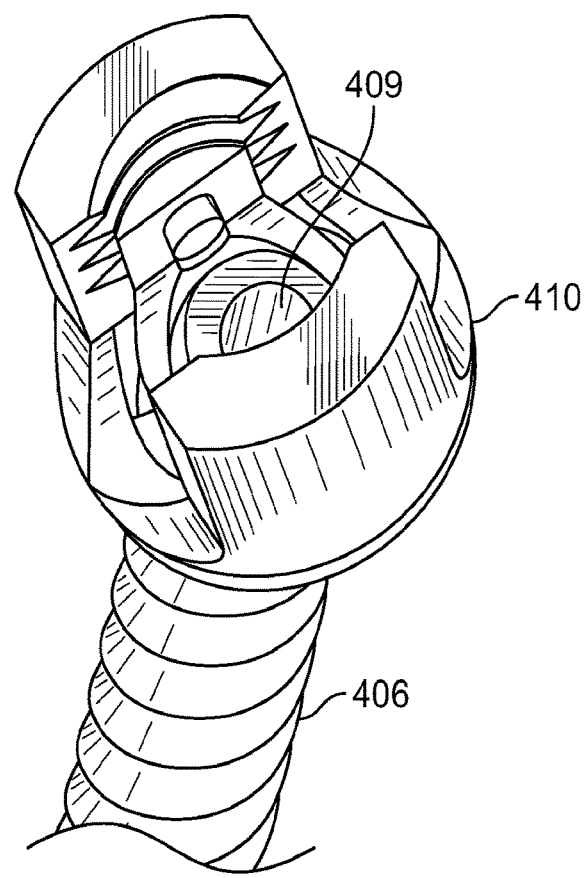
FIG. 13 is a perspective view of the proximal portion of the pedicle screw in a different configuration to FIG. 12.

As indicated above, once the anchor portion 401 has been inserted into the pedicle and the vertebral body, the threaded sleeve 404 can then be inserted, or implanted. The threaded sleeve 404 is inserted into the pedicle and threaded onto the threaded portion 402 of the anchor portion 401. As discussed above, in the implantation of the sleeve 404, a setting tool may be used to stabilize the anchor portion 401. The aperture 409 allows such a setting tool to pass into the proximal end 417 of the threaded sleeve 404, through the passage 1000 and into the internal bore 405. The setting tool can then engage the recess 414 of the anchor portion 401 and hold the anchor portion 401 steady as the threaded sleeve 404 is threaded onto the threaded portion 402 of the anchor portion 401. Also, the setting tool can serve to guide the threaded sleeve 404 as it is threaded onto the threaded portion 402 of the anchor portion 401. In one embodiment, slots 1100, as shown in FIG. 11, may be provided on the sleeve 404, at a location near the junction of the external threads 406 and the sleeve head 408. The slots 1100 can be adapted to engage with another setting tool to aid in threading the sleeve 404 onto the threaded portion 402. Thus, the threaded sleeve 404 can be threaded onto the anchor portion 401 by using a tool engaged with the slots 1100 or, alternatively, the sleeve 404 can be manually implanted by the surgeon.

As discussed above, as the threaded sleeve 404 is screwed onto the anchor portion 401, the external threads 406 engage of the sleeve 404 engage the bone material of the pedicle, such as pedicle 102b as seen in FIG. 16. The bone material provides the screw 400 with purchase within the pedicle and increases the amount of surface area in contact between the screw 400 and the vertebra 100. This engagement between the threads and the bone material further increases resistance to pullout forces.

After the threaded sleeve 404 has been threaded onto the threaded portion 402, the screw head 410 can be engaged with the sleeve head 408. Once placed, the screw head 410 can be swiveled about the sleeve head 408 in view of the ball and socket arrangement as discussed previously. In this way, the screw head 410 can be positioned as needed so as to allow connection to, for example, spinal fixation devices such as rods 206. As known to persons skilled in the art, the rods 206 extend along a portion of the spine spanning two or more vertebrae and are connected thereto so as to stabilize such spinal region.

As will be appreciated, the pedicle screw 400 described herein incorporates a threaded portion that engages bone material, as with known pedicle screws, but also incorporates a further enhancement achieved by the angled or nail portion 403, which results in increased pullout resistance. As discussed above, the pullout resistance offered by the screw 400 described herein can be further enhanced by providing the protrusion 412.

Figures 5A, 5B, 5C:
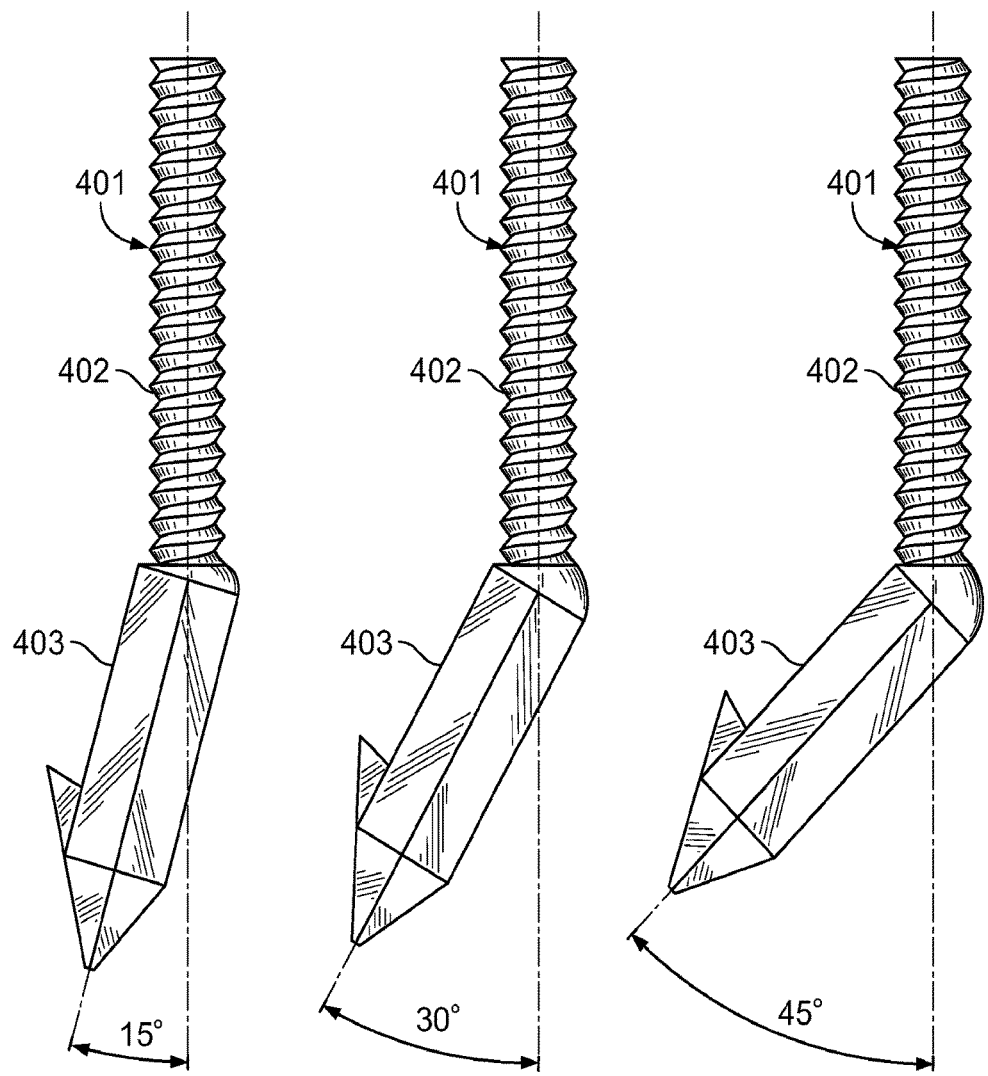
FIGS. 5A-C are side views of the pedicle screw of FIG. 4B in different arrangements.

As will be understood, the present description is not limited to any particular angular configuration of the anchor portion 401. For example, various alternative arrangements are shown in FIGS. 5A-C, wherein angles of 15°, 30° and 45° are illustrated between the angled or nail portion 403 and the threaded portion 402. The present description is not limited to any specific angle of the anchor portion 401.

The screw 400 of the present description can be varied to further enhance pullout resistance. For example, as can be seen in FIGS. 6A and 6B, the angled or nail portion 403*b* of the anchor portion 401 can be provided with one or more rows of raised ridges or spikes etc. 600 positioned along the body of the angled or nail portion 403*b*. As will be understood, the ridges or spikes would serve to further enhance the anchoring of the anchor portion 401 within the bone, particularly once bone re-growth has occurred. In the embodiment shown in FIGS. 6A, 6B and 6C, the raised ridges or spikes are generally pyramidal in shape. However, various other shapes of these features may be used.

FIG. 6C shows exemplary cross sections of the angled or nail portion 403*b* across line B-B of FIG. 6A. A hexagonal cross section 601*a*, pentagonal cross section 601*b*, square or rectangular cross section 601*c* or a triangular cross section 601*d* are different embodiments of the anchor portion 401. The description is not limited to any particular cross sectional shape of the angled or nail portion 403.

Figure 7A:
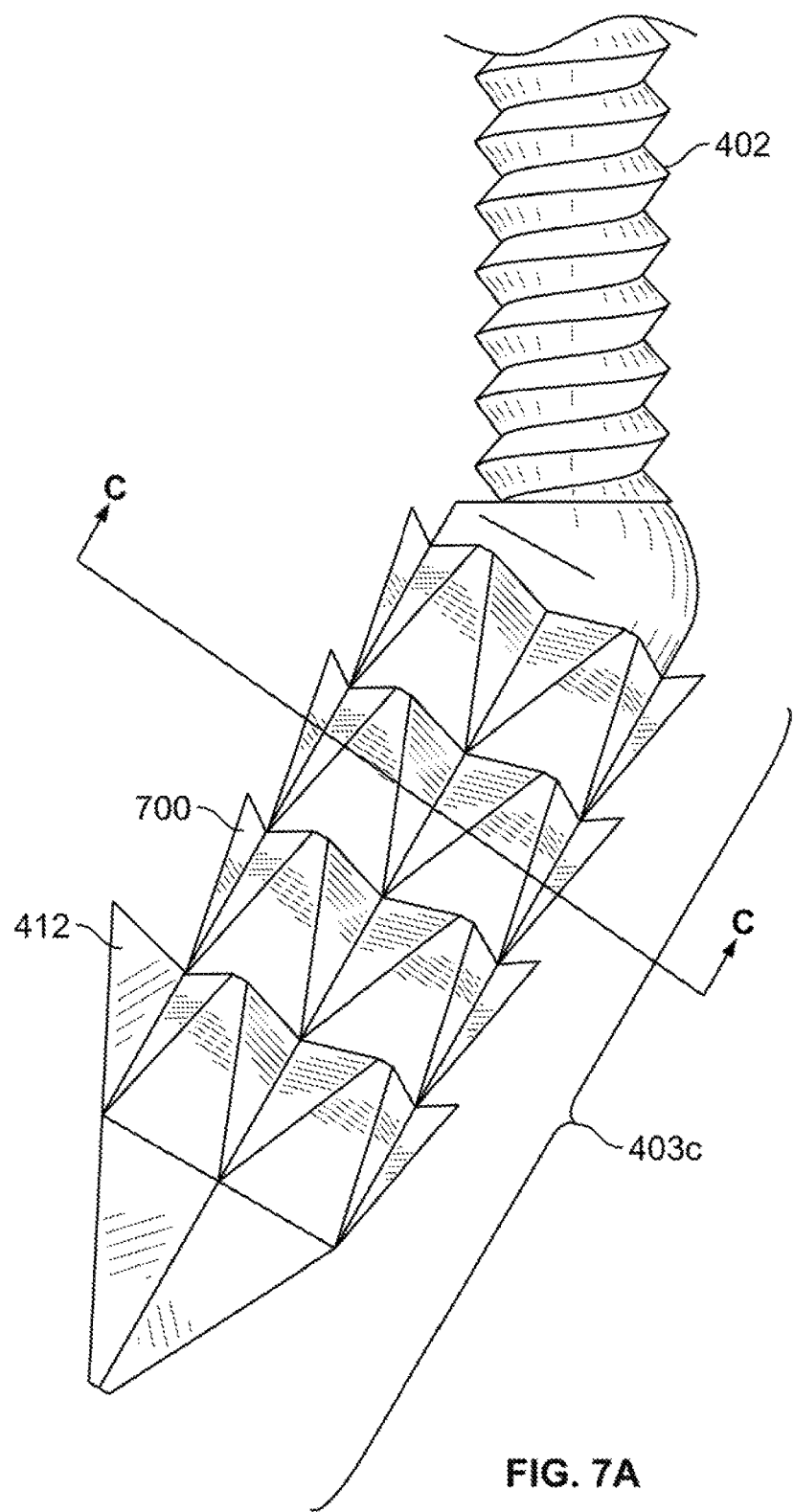
FIG. 7A is a side view of the distal portion of the pedicle screw according to another embodiment.
Figures 7B, 7C:
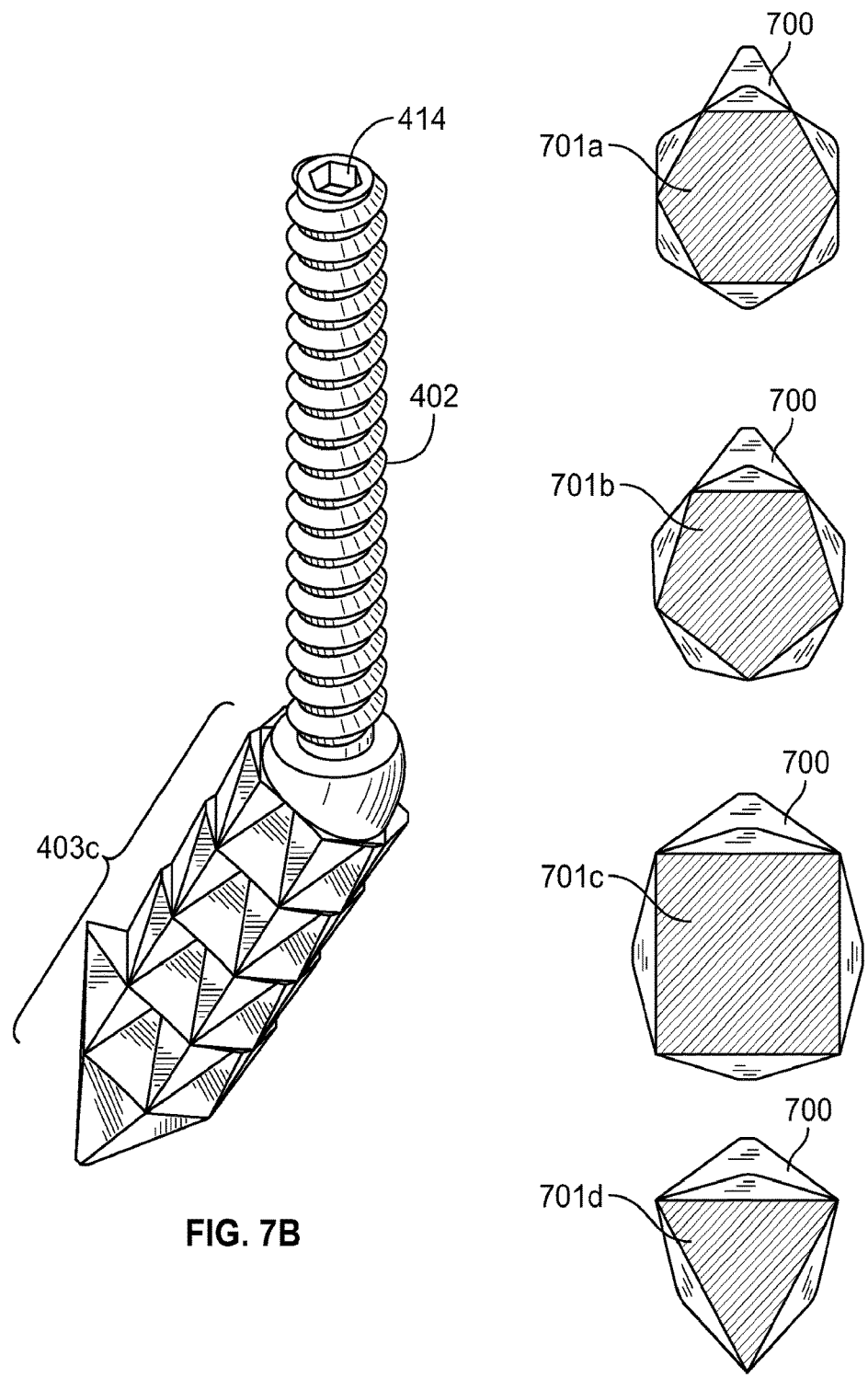
FIG. 7B is a perspective view the pedicle screw of FIG. 7A.
FIG. 7C is a cross sectional view of alternate embodiments for the pedicle screw design of FIG. 7A across the line C-C.

FIGS. 7A and 7B illustrate an alternative to the spikes illustrated in FIGS. 6A, 6B. In this case, the anchor portion 401 has an angled or nail portion 403*c* that is provided with one or more rows of scales 700. As can be seen, the scales project radially outwardly and in a proximal direction, that is away from the distal end of the nail portion.

FIG. 7C shows cross sections across line C-C of the angled or nail portion 403*c*. A hexagonal cross section 701*a*, a pentagon cross section 701*b*, a square or rectangular cross section 701*c* or a triangular cross section 701*d* are all possible as different embodiments of the cross section of angled or nail portion 403*c*.

Figure 8A:
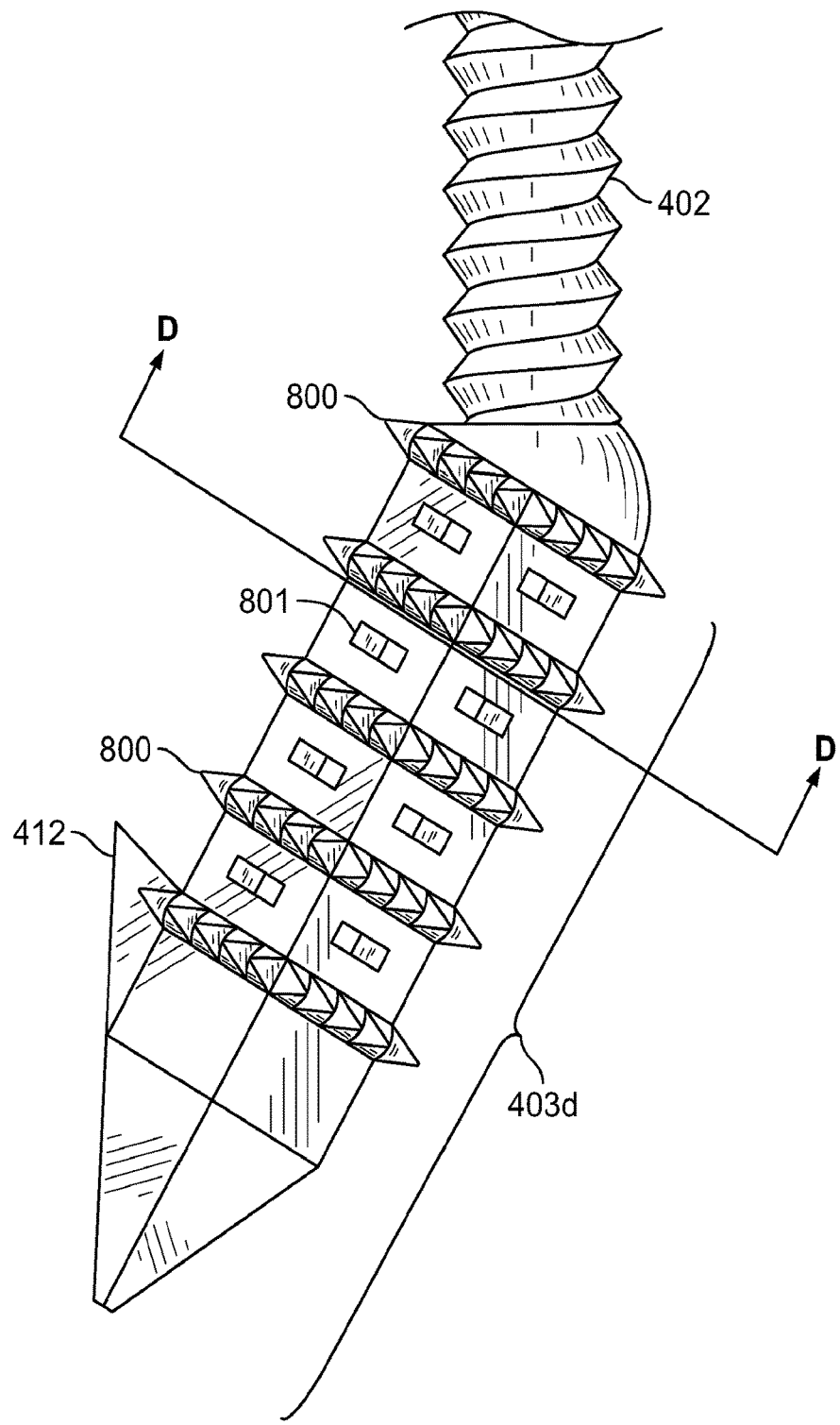
FIG. 8A is a side view of the distal portion of an alternate pedicle screw according to an embodiment.

FIGS. 8A and 8B show yet another embodiment for enhancing the pullout resistance of the screw of the present description. In this embodiment, the angled or nail portion 403*d* of the nail portion is provided with one or more rows of ridges or spikes 800, such as those discussed above. The angled or nail portion 403*d* of FIGS. 8A and 8B is further provided with one or more fenestrations 801. The fenestrations comprise openings into the lumen of the angled or nail portion 403*d*, into which bone is allowed to grow. As will be understood, bone ingrowth into the fenestrations further enhances the grip of the anchor portion 401 in the vertebra 100.

FIG. 8C shows various embodiments of the cross section of the angled or nail portion 403*d* across the line D-D, with hexagonal 802*a*, pentagonal 802*b*, square 802*c* and triangular 802*d* cross sections possible. The shape of the angled or nail portion 403*d* is not limited to these shapes. The course of the fenestrations 801 can also differ with the purpose of promoting bony ingrowth. 801*a* shows the fenestrations in the hexagonal section, 801*b* in the pentagonal section, 801*c* in the square section, 801*d* in the triangular section. The connections between the fenestrations 801 are also variable in depth, number and direction, and can be varied to further facilitate bony ingrowth and allow for greater pullout resistance.

Figure 9A:
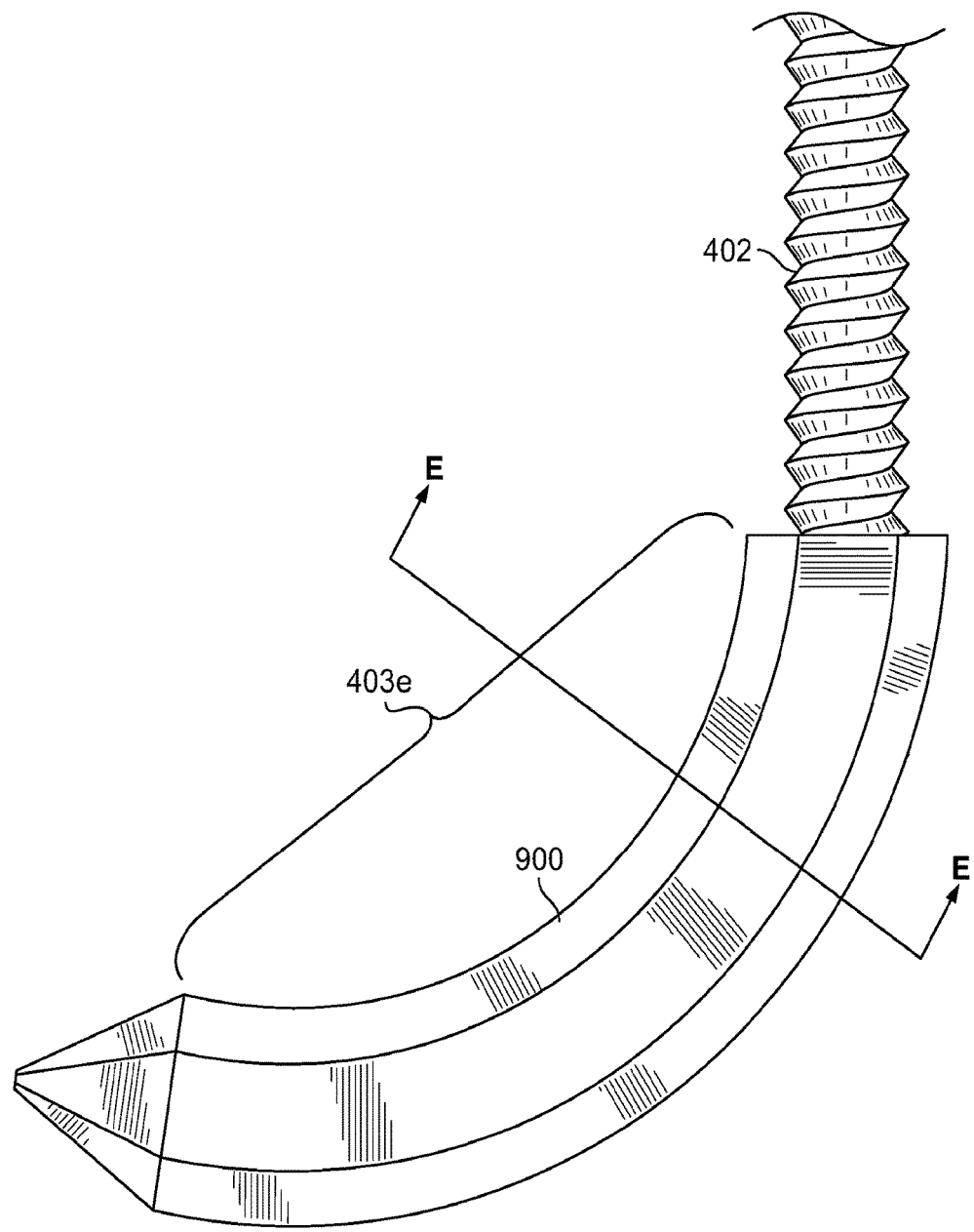
FIG. 9A is a side view of the distal portion of an alternate pedicle screw according to an embodiment.
Figure 9B:
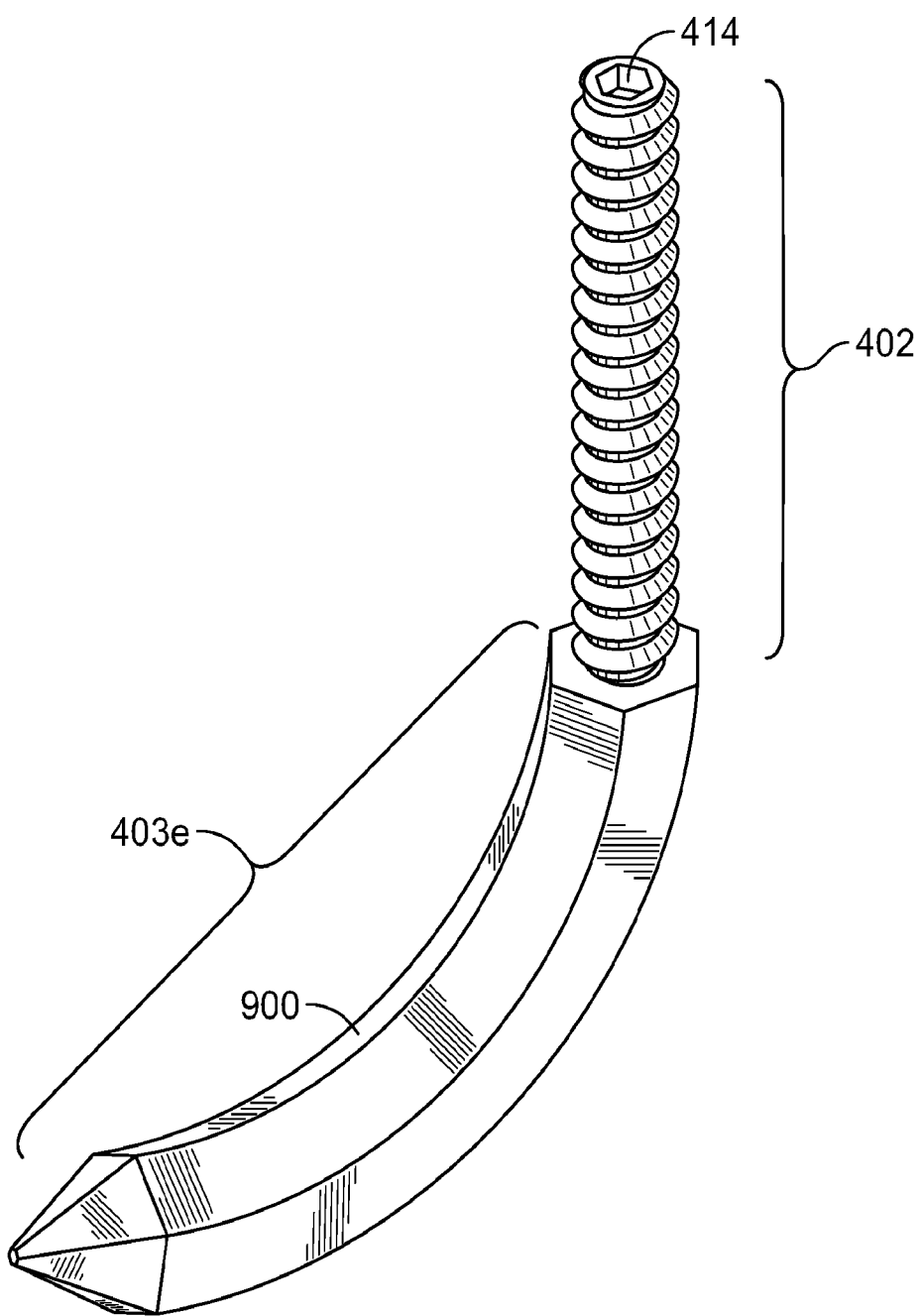
FIG. 9B is a perspective view of the pedicle screw of FIG. 9A.

Another embodiment of the screw described herein is illustrated in FIGS. 9A and 9B, wherein the anchor portion 401 is provided with an angled or nail portion 403*e* that is curved to form a "hook" like arrangement. It will be understood that the surface of the angled or nail portion 403*e* of FIGS. 9A and 9B can be modified as described above to include spikes, scales and/or fenestrations as may be desired or required.

Figure 9C:
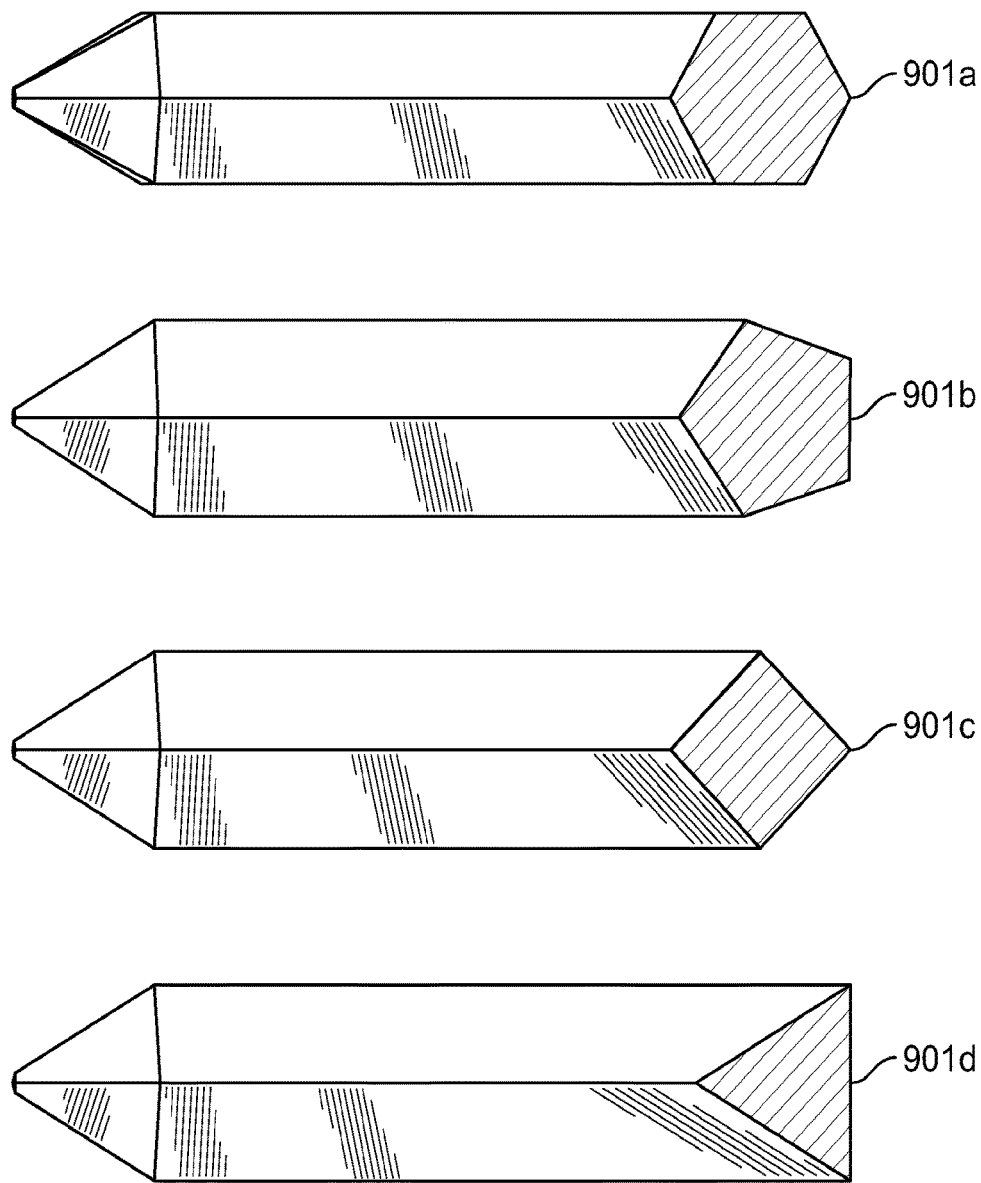
FIG. 9C is a cross sectional view of alternate embodiments for the pedicle screw of FIG. 9A across the line E-E.

As seen in FIG. 9C, the angled or nail portion 403*e* can have varying cross sections across line E-E of the angled or nail portion 403*d*. A hexagonal cross section 901*a*, pentagonal cross section 901*b*, square or rectangular cross section 901*c* or triangular cross section 901*d* are all possible as different embodiments for the cross sectional shape of the angled or nail portion 403*e*.

Figure 14:
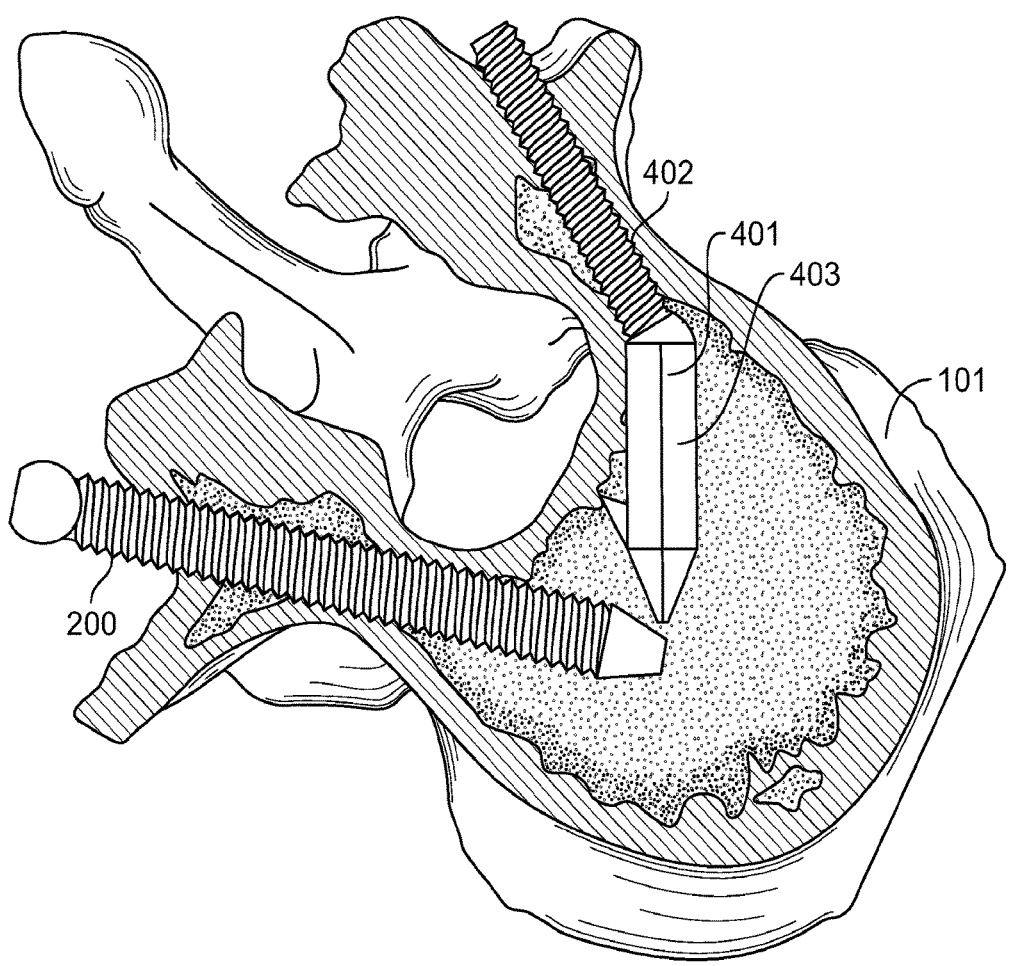
FIG. 14 is a horizontal cross sectional view of a vertebra including a prior art pedicle screw and the pedicle screw of FIG. 4B.
Figure 15:
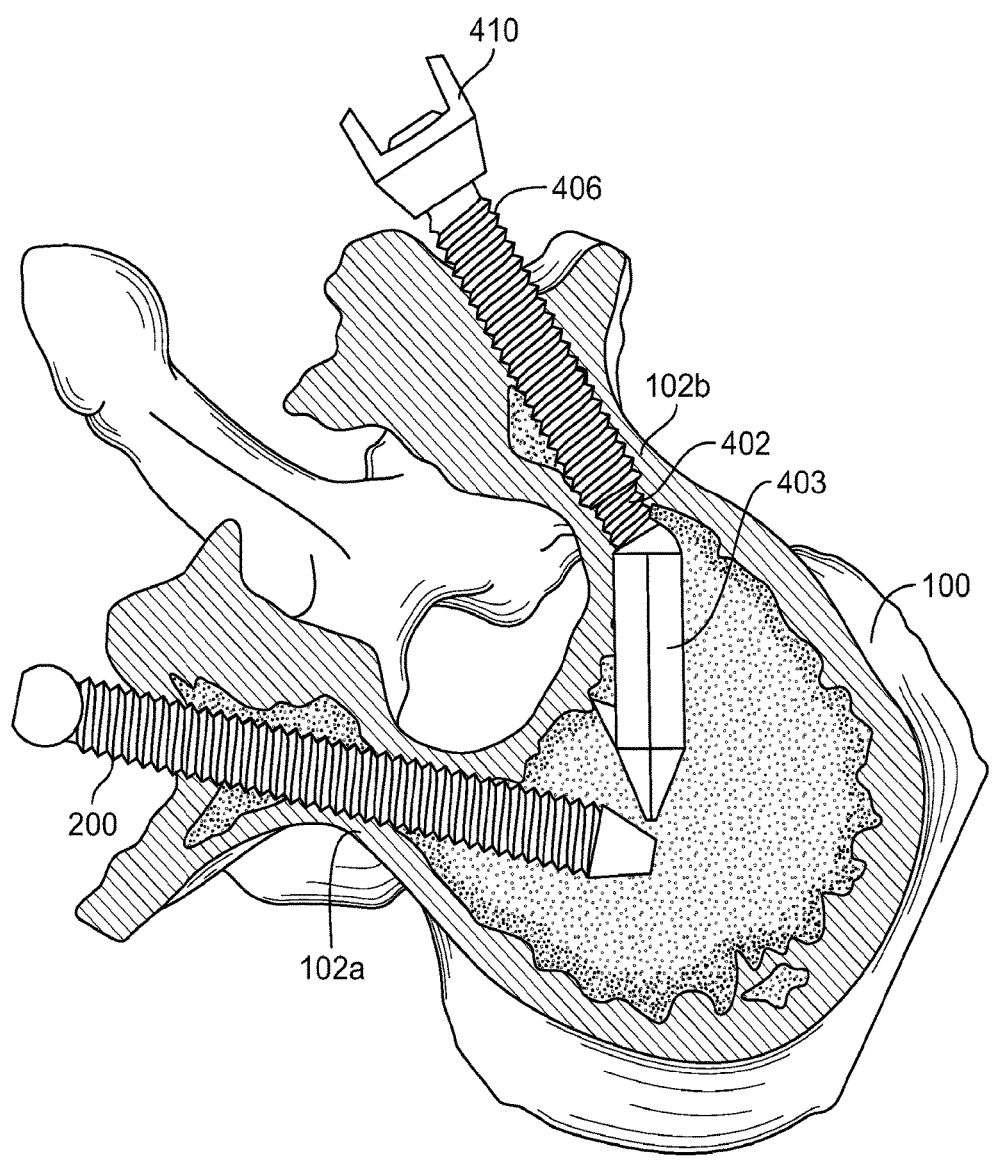
FIG. 15 is a horizontal cross sectional view of a spinal segment incorporating a prior art pedicle and an assembled embodiment of the description.

FIGS. 14 and 15 show the pedicle screw 400 according to an embodiment, as implanted in a vertebra 100. These figures illustrate the difference in how the screw of the description captures bone material over that of known pedicle screws, such as pedicle screw 200.

The external threads 406 of the threaded sleeve 404 also allow purchase with the bone material of the pedicle 1*b*. The presence of the protrusion 412 acts as an anchor into the bone material of vertebra 100 and also increases resistance to pullout. That is, a pedicle screw 200 as known in the art is shown passing straight through the pedicle 102*a* and into the vertebral body 101, whereas the screw 400 according to an embodiment of the description is shown with its angled or nail portion 403 and threaded portion 402 in engagement with the vertebral body 101 and the pedicle 102*b*. As can be seen, the screw 400 contacts and grips more bone material than the known screw 200.

Figures 16A, 16B:
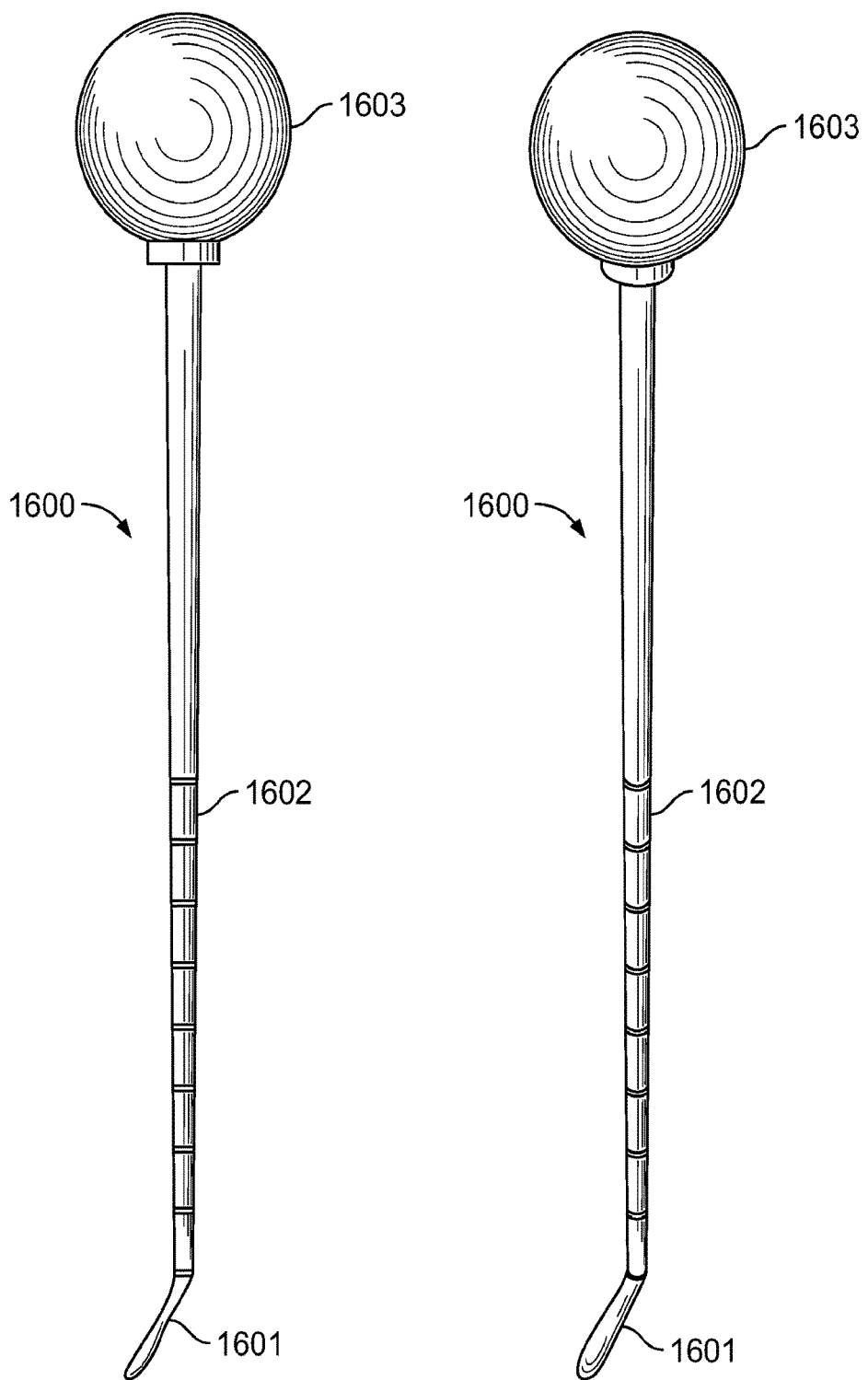
FIG. 16A is a side view of a pedicle tool used in the placement of a pedicle screw embodied in the description.
FIG. 16B is a perspective view of the pedicle tool of FIG. 17A.

As discussed previously a tool such as pedicle probe 1600 shown in FIGS. 16A and 16B, may be used to create a channel into which at least the anchor portion 401 of the screw 400 is inserted or implanted. The probe 1600 is inserted and pushed into the vertebra so as to carve out bone material from the pedicles and the vertebral body 101. The probe 1600 comprises an angled distal portion 1601, a middle portion 1602, and a proximal portion 1603. As illustrated, the distal portion 1601 is preferably angled with respect to the rest of the tool. As will be understood, such an angle allows the aforementioned channel to be formed in a manner that accommodates the angled portion of the anchor portion 401.

Figures 17A, 17B, 17C:
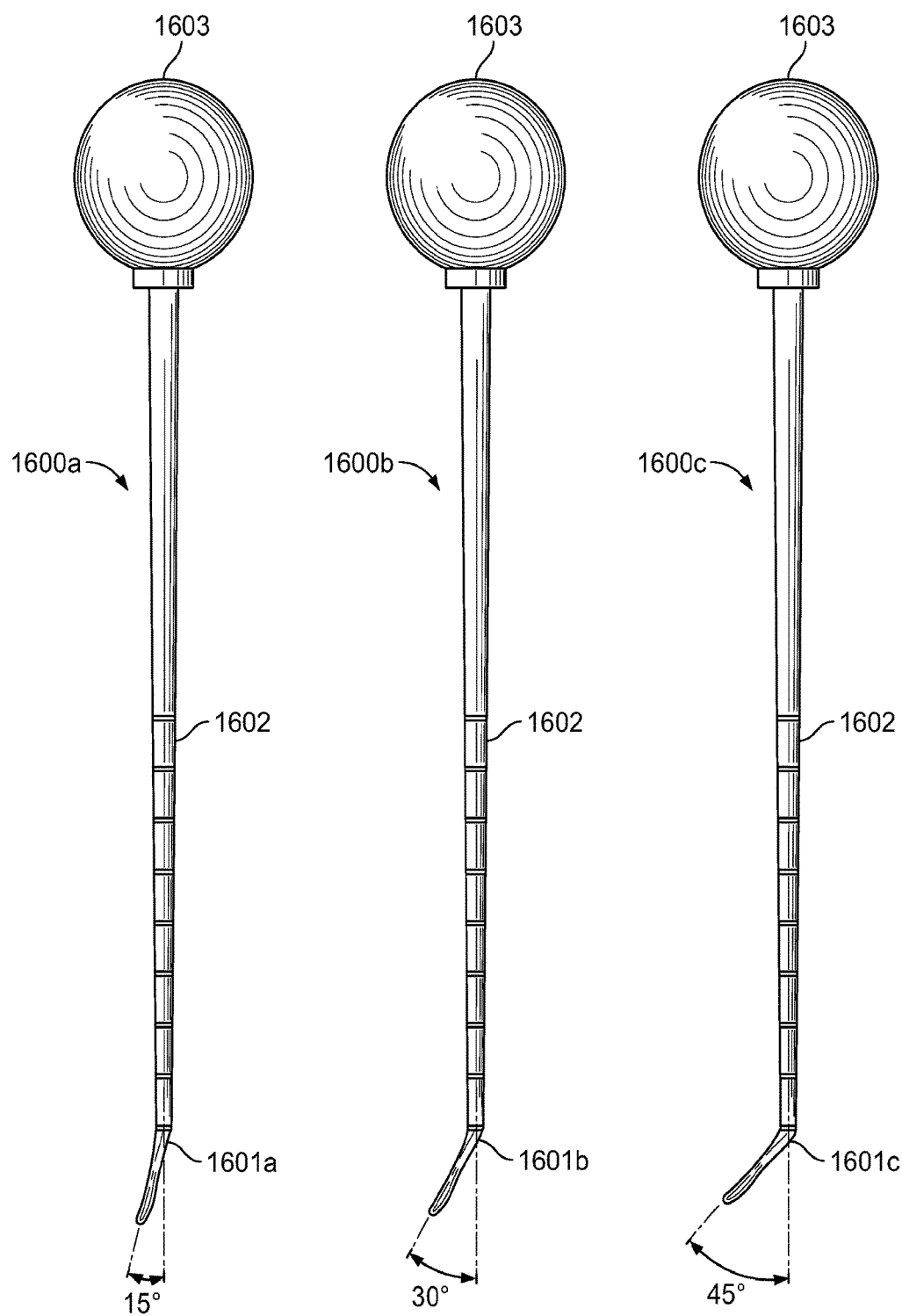
FIGS. 17A-C are side views of the pedicle tool of FIG. 17A in different arrangements.

As can be seen in FIGS. 17A-C pedicle probe 1600 can be provided with any degree of angulation between the distal portion 1601 and the middle portion 1602. As will be understood, the desired pedicle probe may be chosen based on the angle provided on the angled portion 401 of the screw 400.

Figure 19:
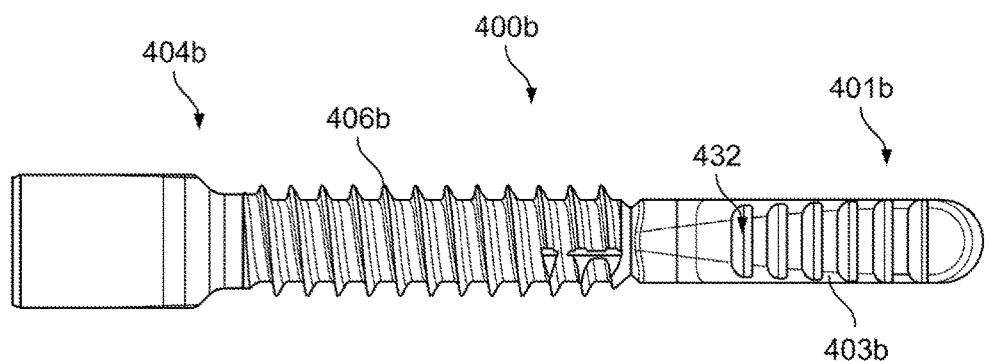
FIG. 19 is a plan view of a bone screw according to another embodiment.
Figure 20:
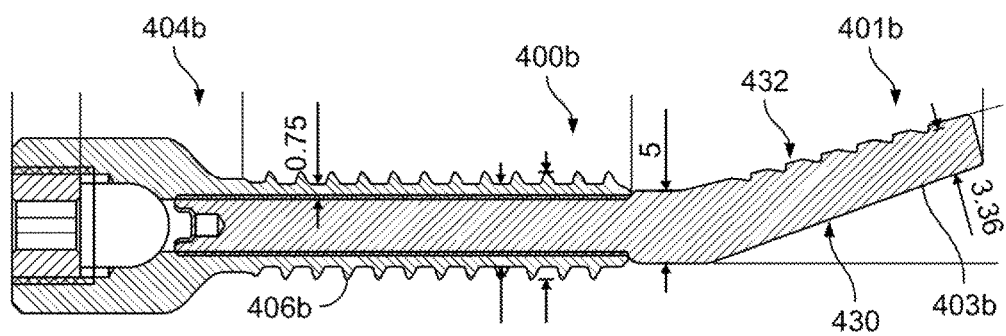
FIG. 20 is a side cross sectional view of the bone screw of FIG. 19.

Another embodiment of the subject bone screw is illustrated in FIGS. 19 and 20, where elements similar to those discussed above are identified with like reference numerals but with the letter "b" added for clarity. As shown, the bone screw 400*b* has a sleeve 404*b* and an anchor (or nail) portion 401*b*. As described above, the anchor portion 401*b* is adapted to be inserted into a cavity formed in bone. The anchor portion 401*b* includes an angled or nail portion 403*b*. In this embodiment, the angled or nail portion 403*b* includes a first surface 430 that is generally smooth and an opposite second surface 432 that includes groove or serrations. As will be understood, the grooves or serrations serve to assist in anchoring the anchor portion 401*b* into bone. Specifically, as bone ingrowth occurs, the new bone material would grow into the serrated portions thereby anchoring the anchor portion. In the embodiment illustrated in FIGS. 19 and 20, the angled or nail portion 403b is optionally provided with a smooth finish on a portion of its outer surface. Such an arrangement would be helpful in the event that the screw, in particular the anchor portion 401b needs to be extracted. In such case, only the serrated portion needs to be extricated from surrounding bone, thereby facilitating removal of the anchor portion 401b. It will be understood that the serrations may optionally be provided over the entire surface of the angled or nail portion 403b or such portion may have no serrations. In the latter case, the angled or nail portion 403b may be provided with other bone adhering finishes or treatments as needed.

The sleeve 404b illustrated in FIGS. 19 and 20 is similar to that described above. Specifically, as shown in FIG. 20, the sleeve 404b includes an inner bore that is adapted to receive at least the proximal end of the anchor portion 401b. As above, a portion of the anchor portion 401b adjacent the proximal end thereof is received within the inner bore of the sleeve 404b. As discussed above, the inner bore of the sleeve 404b and the outer surface of the portion of the anchor portion 401b received within the inner bore are provided with cooperating thread, whereby the sleeve 404b can be screwed onto the anchor portion. The outer surface of the distal portion of the sleeve 404b is provided with threading 406b, which is suitable for being screwed into the bone in question.

Figure 21A:
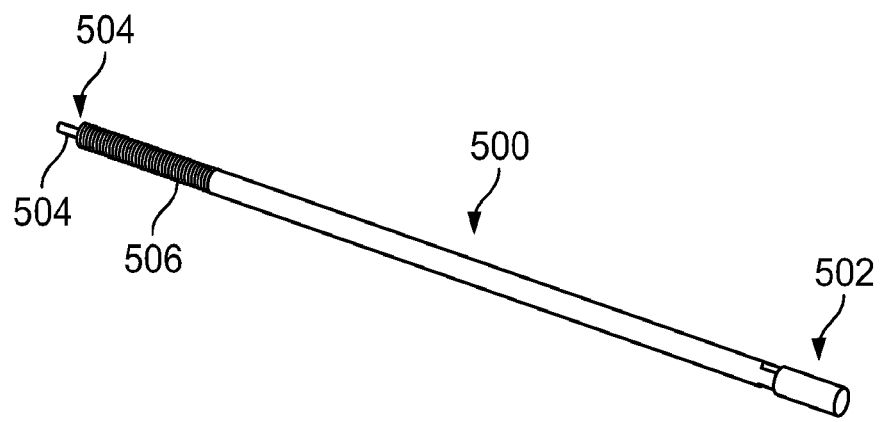
FIGS. 21A to 21H are schematic side views of an embodiment of a bone screw and bone screw system.
Figure 21B:
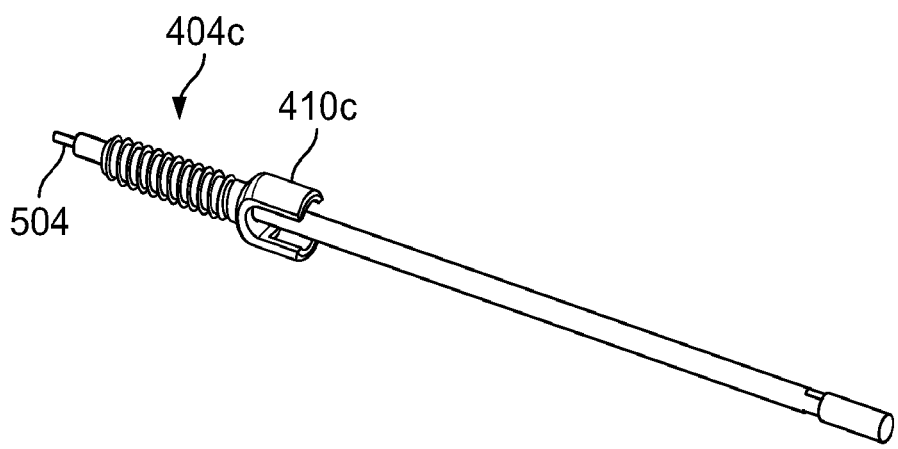

Another embodiment of the bone screw is illustrated in FIGS. 21A to 21H, which also illustrate another embodiment of a bone screw system. In these figures elements similar to those discussed above are identified with like reference numerals but with the letter "c" added for clarity. Further, the anchor portion 401c shown in FIGS. 21A to 21H is similar to the anchor portion 401b discussed above. The embodiment of FIGS. 21A to 21H will now be described in terms of its method of implantation in bone. FIG. 21A illustrates an inserter 500 that is used to assist in the implantation of the bone screw. The inserter 500 comprises an elongate, probe-like structure having a proximal end 502 and a distal end 504. At least a portion of the inserter, adjacent the distal end 504 is provided with a threaded outer surface as shown at 506. In the method of this embodiment, an outer sleeve 404c is combined with the inserter 500. As shown in FIG. 21B, the inserter 500 is inserted through the head 410c and through the bore of the sleeve 404c. Specifically, the distal end 504 of the inserter is inserted through the head 410c and through the proximal end of the sleeve 404c and allowed to protrude through the distal end of the sleeve 404c.

Figure 21C:
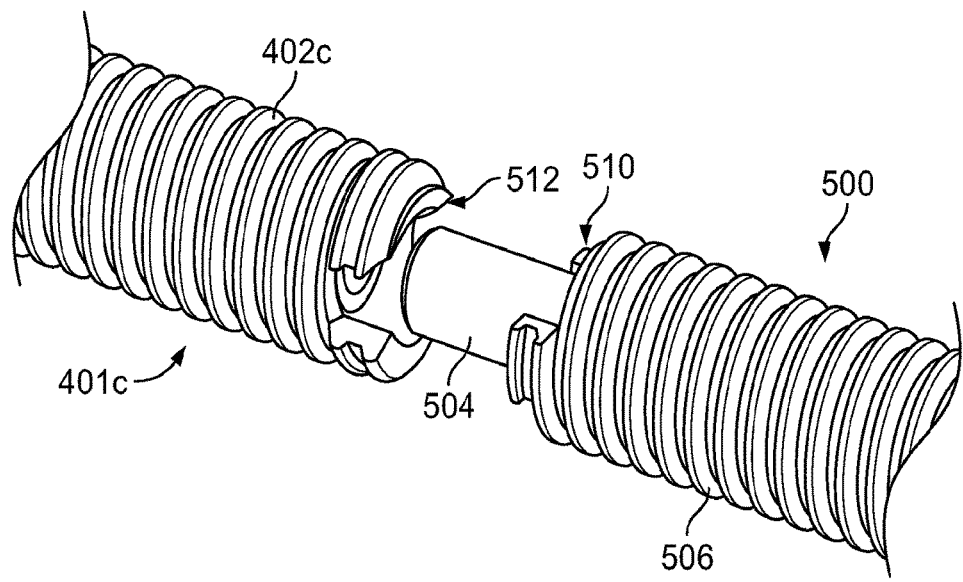

In this embodiment the distal end 504 of the inserter 500 is provided with a probe tip 508 and a first connector portion 510 that forms the distal end of the threading 506. As shown in FIG. 21C, the proximal end 416c of the anchor portion 401c includes a second connector portion 512. The first and second connector portions 510, 512 are adapted to be engaged. For example, in the illustrated embodiment, the first connector portion 510 comprises a pair of tabs and the second connector portion 512 comprises a pair of corresponding slots, which are adapted to receive the tabs of the first connector portion 510. It will be understood that other forms of connection may be used, for the purpose described below.

Figure 21D:
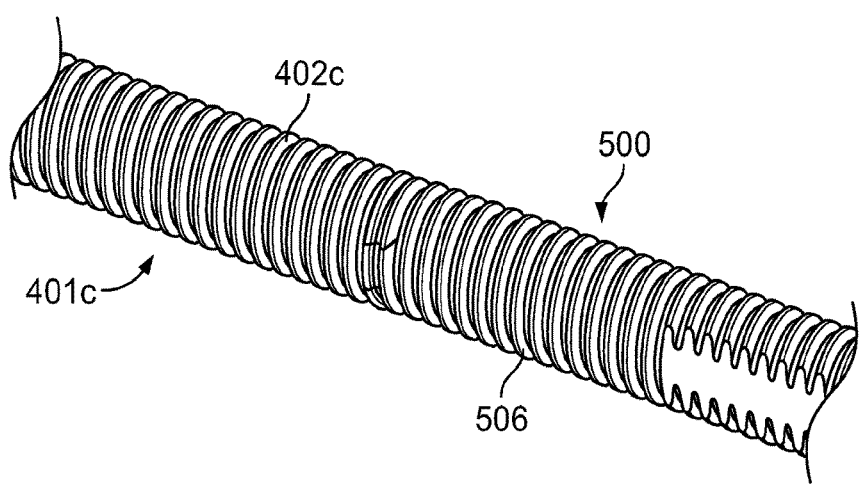

FIG. 21D illustrates the anchor portion 401c and inserter 500 when combined, that is, when the first and second connector portions are engaged.

Figure 21E:
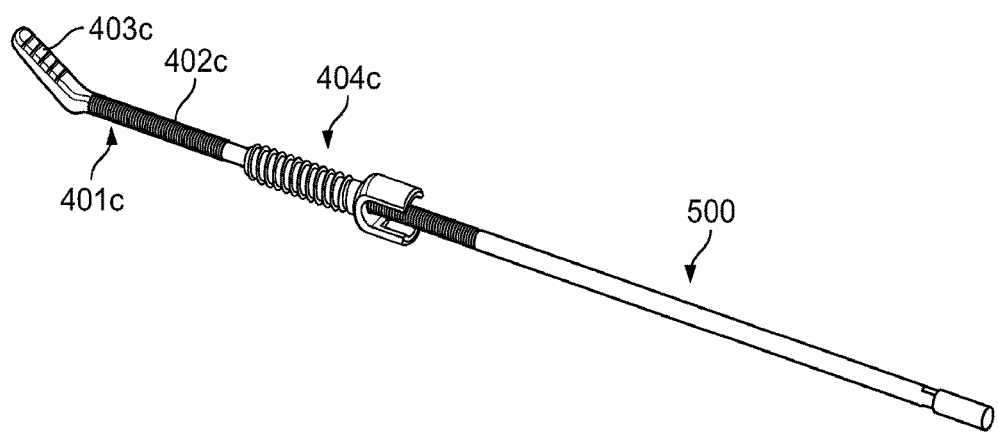
Figure 21F:
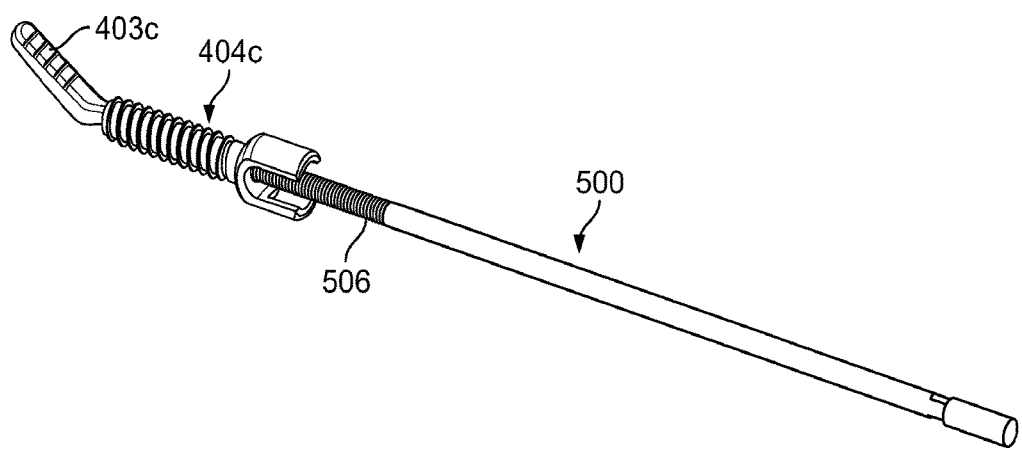
Figure 21G:
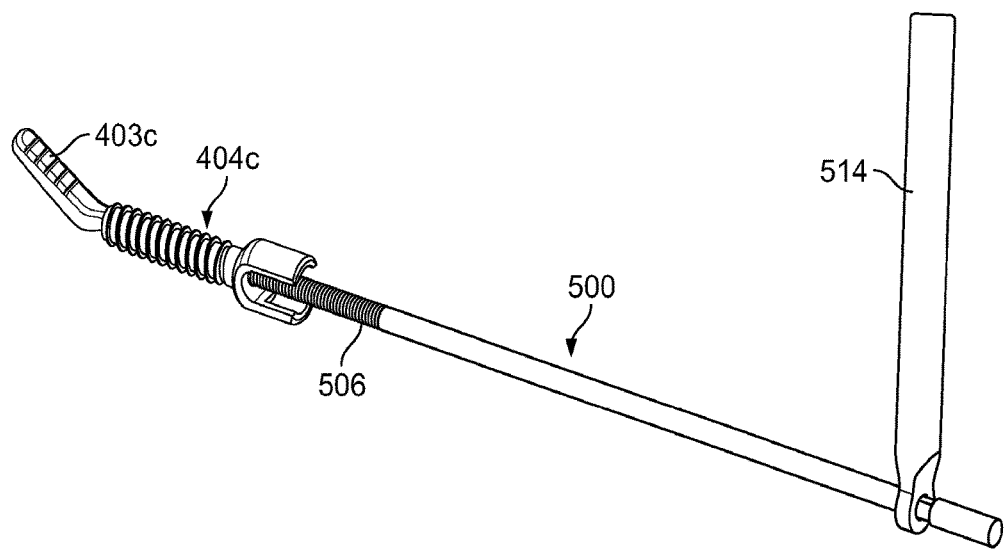

As shown in FIG. 21E, once the inserter 500 is engaged with the anchor portion 401c, the sleeve 404c is slid down the inserter and the thread provided on the inner bore of the sleeve 404c (as described above) is allowed to engage the thread provided on threaded portion 402c of the anchor portion 401c. Such engagement of the sleeve 404c and the anchor portion 401c is similar to the arrangement discussed above. The sleeve 404c is then screwed onto the anchor portion 401c in the same manner as discussed above. Any means may be used to turn the sleeve 404c for securing it to the anchor portion 401c as would be apparent from the present description. FIG. 21F illustrates the system once the sleeve 404c is fully screwed on to the anchor portion 401c. As will be understood, during the step of securing the sleeve 404c on the anchor portion 401c, the inserter 500 can be used to hold and stabilize the anchor portion 401c. In this regard, FIG. 21G illustrates an optional handle 514 that may be used to hold the inserter 500 during the above procedure. Once the sleeve 404c is secured to the anchor portion 401c, the inserter 500 may be removed by disengaging the first and second connector portions.

Figure 21H:
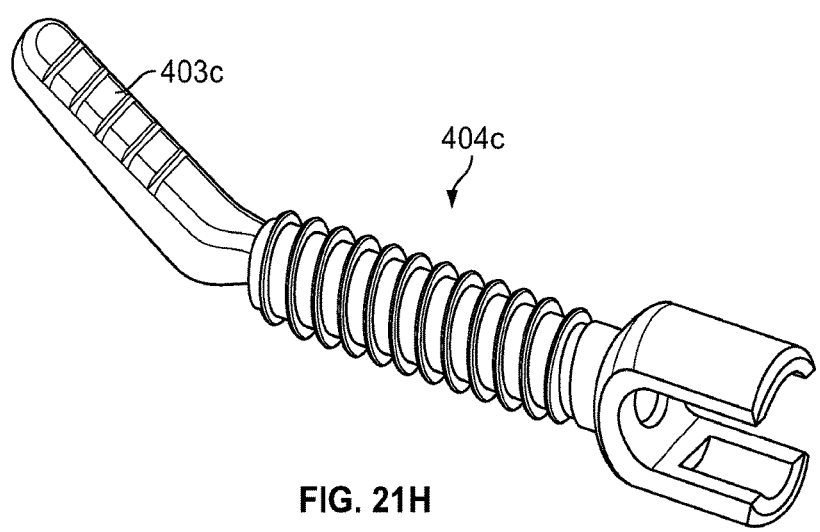

FIG. 21H illustrates the assembled bone screw 400c according to this embodiment as it would appear once implanted and once the inserter is removed. As illustrated and as would be understood, the angled or nail portion 403c of the anchor portion 401c and the threaded portion 406c of the sleeve 404c are exposed to the bone material (which is not shown).

As will be appreciated from the above description, the bone screw described herein provides an improvement over known screws by enhancing the anchoring of the screw to the bone material in which it is implanted.

The screws and screw components of the present description can be made of any material as will be known to persons skilled in the art. For example, the elements of the screw may be made of: metals or metal alloys such as stainless steel, titanium, titanium alloys, nickel-titanium alloys (such as Nitinol™), cobalt-chrome alloys; plastic and/or thermoplastic polymers (such as PEEK™); carbon fiber; or any other material, or combination of materials, commonly associated with bone screws. It will also be understood that the surface of the screws and screw components described herein may optionally be coated with any known substances for improving their placement or adhesion within the bone or for promoting bone ingrowth. For example, in one embodiment, the outer surface of the screw, or at least that portion that will be in contact with bone after implantation, may be coated with hydroxyapatite to promote osseointegration of the screw and, thereby, allowing increased resistance to screw pullout.

Although the above description includes reference to certain specific embodiments, various modifications thereof will be apparent to those skilled in the art. Any examples provided herein are included solely for the purpose of illustration and are not intended to be limiting in any way. Any drawings provided herein are solely for the purpose of illustrating various aspects of the description and are not intended to be drawn to scale or to be limiting in any way. The scope of the claims appended hereto should not be limited by the preferred embodiments set forth in the above description, but should be given the broadest interpretation consistent with the present specification as a whole. The disclosures of all prior art recited herein are incorporated herein by reference in their entirety.

I claim:

1. A bone screw comprising:
   a) an anchor component having first and second ends and comprising a nail portion adjacent the second end and a threaded portion comprising an external thread adjacent the first end, the nail portion and the threaded portion being adapted to be inserted into bone; and, b) a generally cylindrical sleeve component having first and second ends and a bore extending there-through, the bore being threaded over at least a portion thereof adjacent the second end of the sleeve, the sleeve component including a threaded outer surface adjacent at least the second end of the sleeve, the threaded outer surface adapted to be secured into the bone;

wherein the second end of the sleeve component is adapted to receive the first end of the anchor component, and wherein the threaded portion of the anchor component is adapted to engage the threaded bore of the sleeve component; and wherein the nail portion and the threaded portion of the anchor component have respective longitudinal axes, and wherein the longitudinal axis of the nail portion is angled with respect to the longitudinal axis of the threaded portion.

2. The bone screw according to claim 1, wherein the nail portion is adapted to allow bone ingrowth.

3. The bone screw according to claim 2, wherein the nail portion is provided with one or more of serrations, grooves, apertures, scales, and raised portions for allowing bone ingrowth.

4. The bone screw according to claim 1, wherein the first end of the sleeve component includes a head adapted for connection to a bone fixation device.

5. The bone screw according to claim 4, wherein the head is integrally formed with the sleeve component or is connected thereto.

6. The bone screw according to claim 4, wherein the head is adapted to swivel about a longitudinal axis of the sleeve component.

7. The bone screw according to claim 4, wherein the second end of the anchor component is adapted to receive a positioning device to stabilize the anchor component when connecting to the sleeve component.

8. The bone screw according to claim 1, wherein the angle between the longitudinal axes of the nail portion and the threaded portion is between 15 and 45 degrees.

9. The bone screw according to claim 1, wherein the nail portion includes a protrusion for anchoring to bone.

10. The bone screw according to claim 1, wherein the bone screw is a pedicle screw.

11. The bone screw according to claim 4, wherein the bone screw is a pedicle screw.

12. The bone screw according to claim 7, wherein the second end of the anchor component includes a recess for receiving an end of the positioning device.

13. The bone screw according to claim 12, wherein the head of the first end of the sleeve component includes an aperture therethrough for allowing passage of the positioning device.

14. The bone screw according to claim 13, wherein the aperture opens into the bore of the sleeve component.

15. The bone screw according to claim 14, wherein the sleeve component includes one or more recesses adjacent the head for engaging a further setting tool.

16. The bone screw according to claim 1, wherein the outer surface of the screw is provided with physical features or chemical treatment for promoting bone ingrowth and/or adhesion.

17. The bone screw according to claim 4, wherein the outer surface of the screw is provided with physical features or chemical treatment for promoting bone ingrowth and/or adhesion.

* * * * *